United States Patent [19]
Hediger

[11] Patent Number: 5,849,525
[45] Date of Patent: Dec. 15, 1998

[54] COMPOSITIONS CORRESPONDING TO A PROTON-COUPLED PEPTIDE TRANSPORTER AND METHODS OF MAKING AND USING SAME

[75] Inventor: Matthias Hediger, Wellesley, Mass.

[73] Assignee: Brigham and Women's Hospital, Inc., Boston, Mass.

[21] Appl. No.: 576,165

[22] Filed: Dec. 21, 1995

Related U.S. Application Data

[63] Continuation of Ser. No. 208,645, Mar. 9, 1994, abandoned.
[51] Int. Cl.$^6$ ............................ C12N 15/12; C07K 14/47; C07K 14/705; C12P 21/02
[52] U.S. Cl. ........................ 435/69.1; 536/23.5; 530/350; 435/7.2; 435/325
[58] Field of Search ........................... 530/350; 435/69.1, 435/320.1, 252.3, 325, 7.2; 536/23.5

[56] References Cited

U.S. PATENT DOCUMENTS 5,500,346  3/1996  Bright et al. ........................... 435/7.21

OTHER PUBLICATIONS

Yusei Miyamoto et al., The Journal of Biological Chemistry, pp. 4742–4745, vol. 266, No. 8, Mar. 15, 1991, "Functional Expression of the Intestinal Peptide–Proton Co–transporter in Xenopus laevis Oocytes".

Yi–Fang Tsay et al., Cell Press, pp. 705–713, vol. 72, Mar. 12, 1993, "The Herbicide Sensitivity Gene CHL1 of Arabidopsis Encodes a Nitrate–Inducible Nitrate Transporter".

Werner Kramer, et al., Feb. 1992, "Intestinal absorption of β–lactam antibodies and oligopeptides", pp. 923–930, Hoechst Aktiengesellschaft, Frankfurt am Main, Federal Republic of Germany.

Hannelore Daniel et al., J. Clin. Invest., vol. 92, Nov. 1993, pp. 2215–2223, "Transport of β–Lactam Antibiotics in Kidney Brush Border Membrane".

Bai JP et al., Journal of Pharmaceutical Sciences 81(2): 113–6, 1992 Feb., Abstract, "Utilization of peptide carrier system to improve intestinal absorption: targeting prolidase as a prodrug–converting enzyme".

Nature 360:467–461 (03 Dec. 1992), Kamat et al Primary structure and functional characteriaztion of a high–affinity glutaunate transporter.

J. Biol. Chem. 267:649–652, (05 Jan. 1992) Yamauchi et al cloning of a Na–and Cl–dependant betaine transporter that is requlated by hypertonicity.

P.N.A.S. 89:1–5, (Jan. 1992) Tate et al Expression cloning of a Nat–independant neutral amnio acid transporter from vat kidney.

Nature 330:379–381, (26 Nov. 1987) Heliger et al. Expression clousing and cDNA sequency of the Natl glucose co–transporter.

J. Brok Clem, 267:6297–63.1, (25 Mar. 1992) Kuon et al cloning of the cDNA for a Nat/myo–inositol transporter, a hypertonicity stress protein.

*Primary Examiner*—Stephen Walsh
*Assistant Examiner*—Michael D. Pak
*Attorney, Agent, or Firm*—Cesari and McKenna, LLP

[57] ABSTRACT

The present invention relates to nucleic acid and amino acid sequences corresponding to a proton-coupled peptide transporter and methods of making and using such transporter.

4 Claims, 12 Drawing Sheets

```
   1  CCACCTGCCA GGAGCACGTC CCGCCGGCAG TCGCAGGAGC CCTGGGAGCC
  51  GCCGCCATGG GAATGTCCAA ATCACACAGT TTCTTTGGTT ATCCCCTGAG
 101  CATCTTCTTC ATCGTGGTCA ATGAGTTTTG CGAAAGATTT TCCTACTATG
 151  GAATGCGAGC AATCCTGATT CTGTACTTCA CAAATTTCAT CAGCTGGGAT
 201  GATAACCTGT CCACCGCCAT CTACCATACG TTTGTGGCTC TGTGCTACCT
 251  GACGCCAATT CTCGGAGCTC TTATCGCCGA CTCGTGGCTG GGAAAGTTCA
 301  AGACCATTGT GTCGCTCTCC ATTGTCTACA CAATTGGACA AGCAGTCACC
 351  TCAGTAAGCT CCATTAATGA CCTCACAGAC CACAACCATG ATGGCACCCC
 401  CGACAGCCTT CCTGTGCACG TGGTGCTGTC CTTGATCGGC CTGGCCCTGA
 451  TAGCTCTCGG GACTGGAGGA ATCAAACCCT GTGTGTCTGC GTTTGGTGGA
 501  GATCAGTTTG AAGAGGGCCA GGAGAAACAA AGAAACAGAT TTTTTTCCAT
 551  CTTTTACTTG GCTATTAATG CTGGAAGTTT GCTTTCCACA ATCATCACAC
 601  CCATGCTCAG AGTTCAACAA TGTGGAATTC ACAGTAAACA AGCTTGTTAC
 651  CCACTGGCCT TTGGGGTTCC TGCTGCTCTC ATGGCTGTAG CCCTGATTGT
 701  GTTTGTCCTT GGCAGTGGGA TGTACAAGAA GTTCAAGCCA CAGGGCAACA
 751  TCATGGGTAA AGTGGCCAAG TGCATCGGTT TTGCCATCAA AAATAGATTT
 801  AGGCATCGGA GTAAGGCATT TCCCAAGAGG GAGCACTGGC TGGACTGGGC
 851  TAAAGAGAAA TACGATGAGC GGCTCATCTC CCAAATTAAG ATGGTTACGA
 901  GGGTGATGTT CCTGTATATT CCACTCCCAA TGTTCTGGGC CTTGTTTGAC
 951  CAGCAGGGCT CCAGGTCCAC ACTGCAGGCA ACAACTATGT CCGGGAAAAT
1001  CGGAGCTCTT GAAATTCAGC CCGATCAGAT GCAGACCGTG AACGCCATCC
1051  TGATCGTGAT CATGGTCCCG ATCTTCGATG CTGTGCTGTA CCCTCTCATT
1101  GCAAAATGTG GCTTCAATTT CACCTCCTTG AAGAAGATGG CAGTTGGCAT
1151  GGTCCTGGCC TCCATGGCCT TTGTGGTGGC TGCCATCGTG CAGGTGGAAA
1201  TCGATAAAAC TCTTCCAGTC TTCCCCAAAG GAAACGAAGT CCAAATTAAA
1251  GTTTTGAATA TAGGAAACAA TACCATGAAT ATATCTCTTC CTGGAGAGAT
1301  GGTGACACTT GGCCCAATGT CTCAAACAAA TGCATTTATG ACTTTTGATG
1351  TAAACAAACT GACAAGGATA ACATTTCTT CTCCTGGATC ACCAGTCACT
1401  GCTGTAACTG ACGACTTCAA GCAGGGCCAA CGCCACACGC TTCTAGTGTG
1451  GGCCCCCAAT CACTACCAGG TGGTAAAGGA TGGTCTTAAC CAGAAGCCAG
1501  AAAAAGGGGA AAATGGAATC AGATTTGTAA ATACTTTTAA CGAGCTCATC
1551  ACCATCACAA TGAGTGGGAA AGTTTATGCA AACATCAGCA GCTACAATGC
1601  CAGCACATAC CAGTTTTTTC CTTCTGGCAT AAAAGGCTTC ACAATAAGCT
1651  CAACAGAGAT TCCGCCACAA TGTCAACCTA ATTTCAATAC TTTCTACCTT
```

FIG. 1A

```
1701  GAATTTGGTA GTGCTTATAC CTATATAGTC CAAAGGAAGA ATGACAGCTG
1751  CCCTGAAGTG AAGGTGTTTG AACATATTTC AGCCAACACA GTTAACATGG
1801  CTCTGCAAAT CCCGCAGTAT TTTCTTCTCA CCTGTGGCGA AGTGGTCTTC
1851  TCTGTCACGG GATTGGAATT CTCATATTCT CAGGCTCCTT CCAACATGAA
1901  GTCGGTGCTT CAGGCAGGAT GGCTGCTGAC CGTGGCTGTT GGCAACATCA
1951  TTGTGCTCAT CGTGGCAGGG GCAGGCCAGT TCAGCAAACA GTGGGCCGAG
2001  TACATTCTAT TTGCCGCGTT GCTTCTGGTC GTCTGTGTAA TTTTTGCCAT
2051  CATGGCTGCC TTCTATACTT ACATCAACCC AGCGGAGATC GAAGCTCAAT
2101  TTGATGAGGA TGAAAAGAAA AACAGACTGG AAAAGAGTAA CCCATATTTC
2151  ATGTCAGGGG CCAATTCACA GAAACAGATG TGAAGGTCAG GAGGCAAGTG
2201  GAGGATGGAC TGGGCCCGCA GATGCCCTGA CCTCTGCCCC CAGGTAGCAG
2251  GACACTCCAT TGG
```

FIG. 1B

```
  1  MGMSKSHSFF  GYPLSIFFIV  VNEFCERFSY  YGMRAILILY  FTNFISWDDN
 51  LSTAIYHTFV  ALCYLTPILG  ALIADSWLGK  FKTIVSLSIV  YTIGQAVTSV
101  SSINDLTDHN  HDGTPDSLPV  HVVLSLIGLA  LIALGTGGIK  PCVSAFGGDQ
151  FEEGQEKQRN  RFFSIFYLAI  NAGSLLSTII  TPMLRVQQCG  IHSKQACYPL
201  AFGVPAALMA  VALIVFVLGS  EMYKKFKPQG  NIMGKVAKCI  GFAIKNRFRH
251  RSKAFPKREH  WLDWAKEKYD  ERLISQIKMV  TRVMFLYIPL  PMFWALFDQQ
301  GSRWTLQATT  MSGKIGALEI  QPDQMQTVNA  ILIVIMVPIF  DAVLYPLIAK
351  CGFNFTSLKK  MAVGMVLASM  AFVVAAIVQV  EIDKTLPVFP  KGNEVQIKVL
401  NIGNNTMNIS  LPGEMVTLGP  MSQTNAFMTF  DVNKLTRINI  SSPGSPVTAV
451  TDDFKQGQRH  TLLVWAPNHY  QVVKDGLNQK  PEKGENGIRF  VNTFNELITI
501  TMSGKVYANI  SSYNASTYQF  FPSGIKGFTI  SSTEIPPQCQ  PNFNTFYLEF
551  GSAYTYIVQR  KNDSCPEVKV  FEDISANTVN  MALQIPQYFL  LTCGEVVFSV
601  TGLEFSYSQA  PSNMKSVLQA  GWLLTVAVGN  IIVLIVAGAG  QFSKQWAEYI
651  LFAALLLVVC  VIFAIMARFY  TYINPAEIEA  QFDEDEKKNR  LEKSNPYFMS
701  GANSQKQM
```

FIG. 2

```
   1  CCACGCGTCC GAGCCCTAGG AGCAGCCACC ATGGGAATGT CTAAGTCACT
  51  GAGCTGCTTC GGCTATCCCC TGAGCATCTT CTTCATCGTG GTCAATGAGT
 101  TCTGCGAAAG GTTCTCCTAC TATGGGATGA GAGCACTCCT GATTCTGTAC
 151  TTCAGAAACT TCATCGGCTG GACGACAAC CTGTCCACGG TCATCTACCA
 201  CACGTTCGTC GCGCTGTGCT ACCTCACGCC CATTCTCGGA GCTCTCATCG
 251  CCGACGCGTG GCTGGGGAAG TTCAAGACCA TCGTGTGGCT GTCCATCGTC
 301  TACACCATCG ACAAGCAGT CACCTCCCTC AGCTCCGTCA ATGAGCTCAC
 351  AGACAACAAC CATGACGGGA CCCCCGACAG CCTCCCTGTG CACGTGGCGG
 401  TGTGCATGAT CGGCCTGCTC CTGATAGCCC TCGGGACAGG AGGAATCAAG
 451  CCCTGTGTGT CTGCCTTTGG CGGCGATCAG TTTGAGGAGG CCAGGAAAA
 501  GCAAAGAAAC CGGTTTTTTT CCATGTTTTA CTTGGCCATT AACGCTGGGA
 551  GTCTGCTGTC CACAATCATC ACCCCCATGG TCAGAGTTCA ACAATGTGGA
 601  ATTCACGTTA ACAAGCTTG CTACCCACTG GCCTTTGGGA TTCCTGCTAT
 651  CCTCATGGCT GTATCCCTGA TCGTGTTCAT CATCGGCAGT GGGATGTACA
 701  AGAAGTTCAA GCCGCAGGGG AACATCCTGA GCAAAGTGGT GAAGTGCATC
 751  TGCTTTGCCA TCAAAAATAG GTTTAGGCAC CGCAGTAAGC AGTTTCCCAA
 801  GAGGGCGCAC TGGCTGGACT GGGCTAAGGA GAAATACGAC GAGCGGCTTA
 851  TCGCGCAGAT CAAGATGGTT ACGAGGGTGC TGTTCCTGTA CATCCCACTC
 901  CCCATGTTCT GGGCCTTGTT TGATCAGCAG GGTTCCAGAT GGACGCTGCA
 951  AGCGACGACC ATGTCCGGGA GAATTGGAAT CCTTGAAATT CAGCCGGATC
1001  AGATGCAGAC TGTGAACACC ATCTTGATTA TTATCCTGGT CCCCATCATG
1051  GACGCCGTGG TGTATCCTCT GATTGCAAAG TGTGGCCTCA ACTTCACCTC
1101  TCTGAAGAAG ATGACGATTG GATCTTCCT GGCTTCCATG GCCTTCGTGG
1151  CAGCTGCAAT CCTGCAGGTG GAAATCGATA AACTCTTCC TGTCTTCCCC
1201  AAAGCCAATG AAGTCCAAAT TAAAGTTCTG AATGTAGGAA GTGAGAACAT
1251  GATCATCTCT CTTCCTGGGC AGACGGTGAC GCTCAACCAG ATGTCTCAAA
1301  CGAATGAATT CATGACTTTC AATGAAGACA CACTGACAAG CATAAACATC
1351  ACTTCCGGAT CACAAGTCAC CATGATCACA CCCAGCCTTG AGGCAGGCCA
1401  GCGCCACACC CTGCTGGTGT GGGCCCCCAA TAACTACCGA GTGGTCAATG
1451  ACGGCCTGAC CCAGAAGTCA GACAAAGGAG AAAATCCAAT CAGGTTTGTG
1501  AACACTTACA GCCAGCCCAT CAACGTCACG ATGAGCGGGA AGTTTACGA
1551  ACACATCGCC AGCTACAATG CCAGCGAGTA TCAGTTTTTC ACTTCTGGAG
1601  TAAAGGGCTT CACCGTCAGC TCGGCAGGCA TCTCGGAGCA GTGCAGGCGG
1651  GACTTTGAGT CTCCGTACCT GGAGTTTGGC AGCGCGTACA CGTACCTGAT
1701  CACGAGCCAG GCTACTGGCT GCCCCCAAGT GACGGAGTTT GAAGATATTC
```

FIG. 3A

```
1751  CGCCCAACAC AATGAACATG GCTTGGCAAA TCCCACAGTA CTTCCTCATC
1801  ACCTCTGGCG AGGTGGTCTT CTCCATCACG GGCCTGGAGT TCTCCTATTC
1851  TCAGGCTCCT TCCAACATGA AGTCGGTGCT GCAGGCCGGG TGGCTGCTGA
1901  CGGTGGCTGT GGGCAACATC ATTGTGCTCA TCGTGGCCGG CGCGGGCCAG
1951  ATCAACAAGC AGTGGGCCGA GTACATCCTC TTTGCCGCCC TGCTCCTGGT
2001  CGTCTGTGTC ATATTTGCCA TCATGGCTCG ATTCTATACG TATGTCAACC
2051  CGGCCGAGAT CGAGGCTCAG TTTGAAGAAG ATGAGAAGAA AAAGAACCCA
2101  GAAAAGAACG ACCTCTACCC CTCGCTGGCG CCCGTCTCAC AGACACAGAT
2151  GTGAGTCTGG AGGCGGTGTA GGAGGCCCAC GCCTGGCGTG CACTGTGACC
2201  TCTGTCCGAG GGCGCAGGAC GTACCCCTGG GCAGCCCCGG AAGGAGGACT
2251  TGAGAACTGT GAACCAGACC ACGAAAGCTA TGTTCTGAGC AGCCAGTGAT
2301  GAGTCCAAAA CTCTGAAAGA AATCTTGTTG AAAGTCTTAT TTAAAACACA
2351  CACACACACA CACACACACA CACACACTTT TCCAACACTG ACAGCCTACC
2401  CATGTTAACT CCTTCTCTAC CAATGCAAAT GCTGTTATTT TGGACTAACT
2451  TAATTTTGAA CACTGTTCTA TGTTGCTTGT ATTCTAACAT CCTTAGGAAA
2501  GGCAATGTTA AGAGAGGCAG GAGGCAATGC CAAAGTTGAA TATGTAGGTT
2551  TCAGAATGGT ATATACCACA TATTACTTAG TATTAACTGA AAACCTCAAC
2601  TTTGAGGTTT TGTTCTATTT TTTCCACTCC TTACCTCTTT TTAACCTGTG
2651  TACAACTCAA AAGGACCACT CAGATAAAGG CCAGTAAAGA TTTTTTTTGC
2701  CGTTTTGATG AAATAAAATA ATGTTCCTAA GAAAAAAAAA AAAAAA
```

FIG. 3B

```
  1  MGMSKSLSCF  GYPLSIFFIV  VNEFCERFSY  YGMRALLILY  FRNFIGWDDN
 51  LSTVIYHTFV  ALSYLTPILG  ALIADAWLGK  FKTIVWLSIV  YTIGQAVTSL
101  SSVNELTDNN  HDGTPDSLPV  HVAVCMIGLL  LIALGTGGIK  PCVSAFGGDQ
151  FEEGQEKQRN  RFFSIFYLAI  NAGSLLSTII  TPMVRVQQCG  IHVKQACYPL
201  AFGIPAILMA  VSLIVFIIGS  GMYKKFKPQG  NILSKVVKCI  CFAIKNRFRH
251  RSKQFPKRAH  WLDWAKEKYD  ERLIAQIKMV  TRVLFLYIPL  PMFWALFDQQ
301  GSRWTLQATT  MSGRIGILEI  QPDQMQTVNT  ILIIILVPIM  DAVVYPLIAK
351  CGLNFTSLKK  MTIGMFLASM  AFVAAAILQV  EIDKTLPVFP  KANEVQIKVL
401  NVGSENMIIS  LPGQTVTLNQ  MSQTNEFMTF  NEDTLTSINI  TSGSQVTMIT
451  PSLEAGQRHT  LLVWATNNYR  VVNDGLTQKS  DKGENGIRFV  NTYSQPINVT
501  MSGKVYEHIA  SYNASEYQFF  TSGVKGFTVS  SAGISEQCRR  DFESPYLEFG
551  SAYTYLITSQ  ATGCPQVTEF  EDIPPNTMNM  AWQIPQYFLI  TSGEVVFSIT
601  GLEFSYSQAP  SNMKSVLQAG  WLLTVAVGNI  IVLIVAGAGQ  INKQWAEYIL
651  FAALLLVVCV  IFAIMARFYT  YVNPAEIEAQ  FEEDEKKKNP  EKNDLYPSLA
701  PVSQTQM
```

FIG. 4

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2263 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo sapiens ( i x ) FEATURE:
        ( A ) NAME/KEY: CDS ( B ) LOCATION: 57..2183

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| CCACCTGCCA | GGAGCACGTC | CCGCCGGCAG | TCGCAGGAGC | CCTGGGAGCC | GCCGCC | | | | | | | | | | | 56 |

| ATG | GGA | ATG | TCC | AAA | TCA | CAC | AGT | TTC | TTT | GGT | TAT | CCC | CTG | AGC | ATC | 104 |
|---|---|---|---|---|---|---|---|---|---|---|---|---|---|---|---|---|
| Met | Gly | Met | Ser | Lys | Ser | His | Ser | Phe | Phe | Gly | Tyr | Pro | Leu | Ser | Ile | |
| 1 | | | | 5 | | | | | 10 | | | | | 15 | | |

| TTC | TTC | ATC | GTG | GTC | AAT | GAG | TTT | TGC | GAA | AGA | TTT | TCC | TAC | TAT | GGA | 152 |
|---|---|---|---|---|---|---|---|---|---|---|---|---|---|---|---|---|
| Phe | Phe | Ile | Val | Val | Asn | Glu | Phe | Cys | Glu | Arg | Phe | Ser | Tyr | Tyr | Gly | |
| | | | 20 | | | | | 25 | | | | | 30 | | | |

| ATG | CGA | GCA | ATC | CTG | ATT | CTG | TAC | TTC | ACA | AAT | TTC | ATC | AGC | TGG | GAT | 200 |
|---|---|---|---|---|---|---|---|---|---|---|---|---|---|---|---|---|
| Met | Arg | Ala | Ile | Leu | Ile | Leu | Tyr | Phe | Thr | Asn | Phe | Ile | Ser | Trp | Asp | |
| | | 35 | | | | | 40 | | | | | 45 | | | | |

| GAT | AAC | CTG | TCC | ACC | GCC | ATC | TAC | CAT | ACG | TTT | GTG | GCT | CTG | TGC | TAC | 248 |
|---|---|---|---|---|---|---|---|---|---|---|---|---|---|---|---|---|
| Asp | Asn | Leu | Ser | Thr | Ala | Ile | Tyr | His | Thr | Phe | Val | Ala | Leu | Cys | Tyr | |
| | 50 | | | | | 55 | | | | | 60 | | | | | |

| CTG | ACG | CCA | ATT | CTC | GGA | GCT | CTT | ATC | GCC | GAC | TCG | TGG | CTG | GGA | AAG | 296 |
|---|---|---|---|---|---|---|---|---|---|---|---|---|---|---|---|---|
| Leu | Thr | Pro | Ile | Leu | Gly | Ala | Leu | Ile | Ala | Asp | Ser | Trp | Leu | Gly | Lys | |
| 65 | | | | | 70 | | | | | 75 | | | | | 80 | |

| TTC | AAG | ACC | ATT | GTG | TCG | CTC | TCC | ATT | GTC | TAC | ACA | ATT | GGA | CAA | GCA | 344 |
|---|---|---|---|---|---|---|---|---|---|---|---|---|---|---|---|---|
| Phe | Lys | Thr | Ile | Val | Ser | Leu | Ser | Ile | Val | Tyr | Thr | Ile | Gly | Gln | Ala | |
| | | | | 85 | | | | | 90 | | | | | 95 | | |

| GTC | ACC | TCA | GTA | AGC | TCC | ATT | AAT | GAC | CTC | ACA | GAC | CAC | AAC | CAT | GAT | 392 |
|---|---|---|---|---|---|---|---|---|---|---|---|---|---|---|---|---|
| Val | Thr | Ser | Val | Ser | Ser | Ile | Asn | Asp | Leu | Thr | Asp | His | Asn | His | Asp | |
| | | | 100 | | | | | 105 | | | | | 110 | | | |

| GGC | ACC | CCC | GAC | AGC | CTT | CCT | GTG | CAC | GTG | GTG | CTG | TCC | TTG | ATC | GGC | 440 |
|---|---|---|---|---|---|---|---|---|---|---|---|---|---|---|---|---|
| Gly | Thr | Pro | Asp | Ser | Leu | Pro | Val | His | Val | Val | Leu | Ser | Leu | Ile | Gly | |
| | | 115 | | | | | 120 | | | | | 125 | | | | |

| CTG | GCC | CTG | ATA | GCT | CTC | GGG | ACT | GGA | GGA | ATC | AAA | CCC | TGT | GTG | TCT | 488 |
|---|---|---|---|---|---|---|---|---|---|---|---|---|---|---|---|---|
| Leu | Ala | Leu | Ile | Ala | Leu | Gly | Thr | Gly | Gly | Ile | Lys | Pro | Cys | Val | Ser | |
| | 130 | | | | | 135 | | | | | 140 | | | | | |

| GCG | TTT | GGT | GGA | GAT | CAG | TTT | GAA | GAG | GGC | CAG | GAG | AAA | CAA | AGA | AAC | 536 |
|---|---|---|---|---|---|---|---|---|---|---|---|---|---|---|---|---|
| Ala | Phe | Gly | Gly | Asp | Gln | Phe | Glu | Glu | Gly | Gln | Glu | Lys | Gln | Arg | Asn | |
| 145 | | | | | 150 | | | | | 155 | | | | | 160 | |

| AGA | TTT | TTT | TCC | ATC | TTT | TAC | TTG | GCT | ATT | AAT | GCT | GGA | AGT | TTG | CTT | 584 |
|---|---|---|---|---|---|---|---|---|---|---|---|---|---|---|---|---|
| Arg | Phe | Phe | Ser | Ile | Phe | Tyr | Leu | Ala | Ile | Asn | Ala | Gly | Ser | Leu | Leu | |
| | | | | 165 | | | | | 170 | | | | | 175 | | |

| TCC | ACA | ATC | ATC | ACA | CCC | ATG | CTC | AGA | GTT | CAA | CAA | TGT | GGA | ATT | CAC | 632 |
|---|---|---|---|---|---|---|---|---|---|---|---|---|---|---|---|---|
| Ser | Thr | Ile | Ile | Thr | Pro | Met | Leu | Arg | Val | Gln | Gln | Cys | Gly | Ile | His | |
| | | | 180 | | | | | 185 | | | | | 190 | | | |

| AGT | AAA | CAA | GCT | TGT | TAC | CCA | CTG | GCC | TTT | GGG | GTT | CCT | GCT | GCT | CTC | 680 |
|---|---|---|---|---|---|---|---|---|---|---|---|---|---|---|---|---|
| Ser | Lys | Gln | Ala | Cys | Tyr | Pro | Leu | Ala | Phe | Gly | Val | Pro | Ala | Ala | Leu | |
| | | 195 | | | | | 200 | | | | | 205 | | | | |

| ATG | GCT | GTA | GCC | CTG | ATT | GTG | TTT | GTC | CTT | GGC | AGT | GGG | ATG | TAC | AAG | 728 |
|---|---|---|---|---|---|---|---|---|---|---|---|---|---|---|---|---|
| Met | Ala | Val | Ala | Leu | Ile | Val | Phe | Val | Leu | Gly | Ser | Gly | Met | Tyr | Lys | |
| | 210 | | | | | 215 | | | | | 220 | | | | | |

| AAG | TTC | AAG | CCA | CAG | GGC | AAC | ATC | ATG | GGT | AAA | GTG | GCC | AAG | TGC | ATC | 776 |
|---|---|---|---|---|---|---|---|---|---|---|---|---|---|---|---|---|
| Lys | Phe | Lys | Pro | Gln | Gly | Asn | Ile | Met | Gly | Lys | Val | Ala | Lys | Cys | Ile | |
| 225 | | | | | 230 | | | | | 235 | | | | | 240 | |

| GGT | TTT | GCC | ATC | AAA | AAT | AGA | TTT | AGG | CAT | CGG | AGT | AAG | GCA | TTT | CCC | 824 |
|---|---|---|---|---|---|---|---|---|---|---|---|---|---|---|---|---|
| Gly | Phe | Ala | Ile | Lys | Asn | Arg | Phe | Arg | His | Arg | Ser | Lys | Ala | Phe | Pro | |
| | | | | 245 | | | | | 250 | | | | | 255 | | |

| AAG | AGG | GAG | CAC | TGG | CTG | GAC | TGG | GCT | AAA | GAG | AAA | TAC | GAT | GAG | CGG | 872 |
|---|---|---|---|---|---|---|---|---|---|---|---|---|---|---|---|---|
| Lys | Arg | Glu | His | Trp | Leu | Asp | Trp | Ala | Lys | Glu | Lys | Tyr | Asp | Glu | Arg | |
| | | | 260 | | | | | 265 | | | | | 270 | | | |

| CTC | ATC | TCC | CAA | ATT | AAG | ATG | GTT | ACG | AGG | GTG | ATG | TTC | CTG | TAT | ATT | 920 |
|---|---|---|---|---|---|---|---|---|---|---|---|---|---|---|---|---|
| Leu | Ile | Ser | Gln | Ile | Lys | Met | Val | Thr | Arg | Val | Met | Phe | Leu | Tyr | Ile | |
| | | 275 | | | | | 280 | | | | | 285 | | | | |

| CCA | CTC | CCA | ATG | TTC | TGG | GCC | TTG | TTT | GAC | CAG | CAG | GGC | TCC | AGG | TGG | 968 |
|---|---|---|---|---|---|---|---|---|---|---|---|---|---|---|---|---|
| Pro | Leu | Pro | Met | Phe | Trp | Ala | Leu | Phe | Asp | Gln | Gln | Gly | Ser | Arg | Trp | |

-continued

```
            290                           295                            300
ACA CTG CAG GCA ACA ACT ATG TCC GGG AAA ATC GGA GCT CTT GAA ATT       1016
Thr Leu Gln Ala Thr Thr Met Ser Gly Lys Ile Gly Ala Leu Glu Ile
305                 310                 315                 320

CAG CCC GAT CAG ATG CAG ACC GTG AAC GCC ATC CTG ATC GTG ATC ATG       1064
Gln Pro Asp Gln Met Gln Thr Val Asn Ala Ile Leu Ile Val Ile Met
            325                 330                 335

GTC CCG ATC TTC GAT GCT GTG CTG TAC CCT CTC ATT GCA AAA TGT GGC       1112
Val Pro Ile Phe Asp Ala Val Leu Tyr Pro Leu Ile Ala Lys Cys Gly
        340                 345                 350

TTC AAT TTC ACC TCC TTG AAG AAG ATG GCA GTT GGC ATG GTC CTG GCC       1160
Phe Asn Phe Thr Ser Leu Lys Lys Met Ala Val Gly Met Val Leu Ala
            355                 360                 365

TCC ATG GCC TTT GTG GTG GCT GCC ATC GTG CAG GTG GAA ATC GAT AAA       1208
Ser Met Ala Phe Val Val Ala Ala Ile Val Gln Val Glu Ile Asp Lys
370                 375                 380

ACT CTT CCA GTC TTC CCC AAA GGA AAC GAA GTC CAA ATT AAA GTT TTG       1256
Thr Leu Pro Val Phe Pro Lys Gly Asn Glu Val Gln Ile Lys Val Leu
385                 390                 395                 400

AAT ATA GGA AAC AAT ACC ATG AAT ATA TCT CTT CCT GGA GAG ATG GTG       1304
Asn Ile Gly Asn Asn Thr Met Asn Ile Ser Leu Pro Gly Glu Met Val
                405                 410                 415

ACA CTT GGC CCA ATG TCT CAA ACA AAT GCA TTT ATG ACT TTT GAT GTA       1352
Thr Leu Gly Pro Met Ser Gln Thr Asn Ala Phe Met Thr Phe Asp Val
            420                 425                 430

AAC AAA CTG ACA AGG ATA AAC ATT TCT TCT CCT GGA TCA CCA GTC ACT       1400
Asn Lys Leu Thr Arg Ile Asn Ile Ser Ser Pro Gly Ser Pro Val Thr
        435                 440                 445

GCT GTA ACT GAC GAC TTC AAG CAG GGC CAA CGC CAC ACG CTT CTA GTG       1448
Ala Val Thr Asp Asp Phe Lys Gln Gly Gln Arg His Thr Leu Leu Val
    450                 455                 460

TGG GCC CCC AAT CAC TAC CAG GTG GTA AAG GAT GGT CTT AAC CAG AAG       1496
Trp Ala Pro Asn His Tyr Gln Val Val Lys Asp Gly Leu Asn Gln Lys
465                 470                 475                 480

CCA GAA AAA GGG GAA AAT GGA ATC AGA TTT GTA AAT ACT TTT AAC GAG       1544
Pro Glu Lys Gly Glu Asn Gly Ile Arg Phe Val Asn Thr Phe Asn Glu
                485                 490                 495

CTC ATC ACC ATC ACA ATG AGT GGG AAA GTT TAT GCA AAC ATC AGC AGC       1592
Leu Ile Thr Ile Thr Met Ser Gly Lys Val Tyr Ala Asn Ile Ser Ser
            500                 505                 510

TAC AAT GCC AGC ACA TAC CAG TTT TTT CCT TCT GGC ATA AAA GGC TTC       1640
Tyr Asn Ala Ser Thr Tyr Gln Phe Phe Pro Ser Gly Ile Lys Gly Phe
        515                 520                 525

ACA ATA AGC TCA ACA GAG ATT CCG CCA CAA TGT CAA CCT AAT TTC AAT       1688
Thr Ile Ser Ser Thr Glu Ile Pro Pro Gln Cys Gln Pro Asn Phe Asn
    530                 535                 540

ACT TTC TAC CTT GAA TTT GGT AGT GCT TAT ACC TAT ATA GTC CAA AGG       1736
Thr Phe Tyr Leu Glu Phe Gly Ser Ala Tyr Thr Tyr Ile Val Gln Arg
545                 550                 555                 560

AAG AAT GAC AGC TGC CCT GAA GTG AAG GTG TTT GAA GAT ATT TCA GCC       1784
Lys Asn Asp Ser Cys Pro Glu Val Lys Val Phe Glu Asp Ile Ser Ala
                565                 570                 575

AAC ACA GTT AAC ATG GCT CTG CAA ATC CCG CAG TAT TTT CTT CTC ACC       1832
Asn Thr Val Asn Met Ala Leu Gln Ile Pro Gln Tyr Phe Leu Leu Thr
            580                 585                 590

TGT GGC GAA GTG GTC TTC TCT GTC ACG GGA TTG GAA TTC TCA TAT TCT       1880
Cys Gly Glu Val Val Phe Ser Val Thr Gly Leu Glu Phe Ser Tyr Ser
        595                 600                 605

CAG GCT CCT TCC AAC ATG AAG TCG GTG CTT CAG GCA GGA TGG CTG CTG       1928
Gln Ala Pro Ser Asn Met Lys Ser Val Leu Gln Ala Gly Trp Leu Leu
```

```
                610                       615                     620
ACC  GTG  GCT  GTT  GGC  AAC  ATC  ATT  GTG  CTC  ATC  GTG  GCA  GGG  GCA  GGC   1976
Thr  Val  Ala  Val  Gly  Asn  Ile  Ile  Val  Leu  Ile  Val  Ala  Gly  Ala  Gly
625                      630                      635                      640

CAG  TTC  AGC  AAA  CAG  TGG  GCC  GAG  TAC  ATT  CTA  TTT  GCC  GCG  TTG  CTT   2024
Gln  Phe  Ser  Lys  Gln  Trp  Ala  Glu  Tyr  Ile  Leu  Phe  Ala  Ala  Leu  Leu
                    645                      650                           655

CTG  GTC  GTC  TGT  GTA  ATT  TTT  GCC  ATC  ATG  GCT  CGG  TTC  TAT  ACT  TAC   2072
Leu  Val  Val  Cys  Val  Ile  Phe  Ala  Ile  Met  Ala  Arg  Phe  Tyr  Thr  Tyr
               660                      665                      670

ATC  AAC  CCA  GCG  GAG  ATC  GAA  GCT  CAA  TTT  GAT  GAG  GAT  GAA  AAG  AAA   2120
Ile  Asn  Pro  Ala  Glu  Ile  Glu  Ala  Gln  Phe  Asp  Glu  Asp  Glu  Lys  Lys
               675                      680                      685

AAC  AGA  CTG  GAA  AAG  AGT  AAC  CCA  TAT  TTC  ATG  TCA  GGG  GCC  AAT  TCA   2168
Asn  Arg  Leu  Glu  Lys  Ser  Asn  Pro  Tyr  Phe  Met  Ser  Gly  Ala  Asn  Ser
     690                      695                      700

CAG  AAA  CAG  ATG  TGAAGGTCAG  GAGGCAAGTG  GAGGATGGAC  TGGGCCCGCA              2220
Gln  Lys  Gln  Met
705

GATGCCCTGA  CCTCTGCCCC  CAGGTAGCAG  GACACTCCAT  TGG                             2263
```

( 2 ) INFORMATION FOR SEQ ID NO:2:

( i ) SEQUENCE CHARACTERISTICS:
        ( A ) LENGTH: 708 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Gly  Met  Ser  Lys  Ser  His  Ser  Phe  Phe  Gly  Tyr  Pro  Leu  Ser  Ile
1                   5                   10                      15

Phe  Phe  Ile  Val  Val  Asn  Glu  Phe  Cys  Glu  Arg  Phe  Ser  Tyr  Tyr  Gly
               20                      25                      30

Met  Arg  Ala  Ile  Leu  Ile  Leu  Tyr  Phe  Thr  Asn  Phe  Ile  Ser  Trp  Asp
          35                      40                      45

Asp  Asn  Leu  Ser  Thr  Ala  Ile  Tyr  His  Thr  Phe  Val  Ala  Leu  Cys  Tyr
     50                      55                      60

Leu  Thr  Pro  Ile  Leu  Gly  Ala  Leu  Ile  Ala  Asp  Ser  Trp  Leu  Gly  Lys
65                      70                      75                          80

Phe  Lys  Thr  Ile  Val  Ser  Leu  Ser  Ile  Val  Tyr  Thr  Ile  Gly  Gln  Ala
                    85                      90                      95

Val  Thr  Ser  Val  Ser  Ser  Ile  Asn  Asp  Leu  Thr  Asp  His  Asn  His  Asp
                    100                     105                     110

Gly  Thr  Pro  Asp  Ser  Leu  Pro  Val  His  Val  Val  Leu  Ser  Leu  Ile  Gly
               115                     120                     125

Leu  Ala  Leu  Ile  Ala  Leu  Gly  Thr  Gly  Gly  Ile  Lys  Pro  Cys  Val  Ser
     130                     135                     140

Ala  Phe  Gly  Gly  Asp  Gln  Phe  Glu  Glu  Gly  Gln  Glu  Lys  Gln  Arg  Asn
145                     150                     155                      160

Arg  Phe  Phe  Ser  Ile  Phe  Tyr  Leu  Ala  Ile  Asn  Ala  Gly  Ser  Leu  Leu
                    165                     170                     175

Ser  Thr  Ile  Ile  Thr  Pro  Met  Leu  Arg  Val  Gln  Gln  Cys  Gly  Ile  His
               180                     185                     190

Ser  Lys  Gln  Ala  Cys  Tyr  Pro  Leu  Ala  Phe  Gly  Val  Pro  Ala  Ala  Leu
          195                     200                     205

Met  Ala  Val  Ala  Leu  Ile  Val  Phe  Val  Leu  Gly  Ser  Gly  Met  Tyr  Lys
```

|     |     |     | 210 |     |     |     |     | 215 |     |     |     |     | 220 |     |
|-----|-----|-----|-----|-----|-----|-----|-----|-----|-----|-----|-----|-----|-----|-----|

Lys Phe Lys Pro Gln Gly Asn Ile Met Gly Lys Val Ala Lys Cys Ile
225                     230                 235                 240

Gly Phe Ala Ile Lys Asn Arg Phe Arg His Arg Ser Lys Ala Phe Pro
            245                 250                 255

Lys Arg Glu His Trp Leu Asp Trp Ala Lys Glu Lys Tyr Asp Glu Arg
                260                 265                 270

Leu Ile Ser Gln Ile Lys Met Val Thr Arg Val Met Phe Leu Tyr Ile
            275                 280                 285

Pro Leu Pro Met Phe Trp Ala Leu Phe Asp Gln Gly Ser Arg Trp
    290                 295                 300

Thr Leu Gln Ala Thr Thr Met Ser Gly Lys Ile Gly Ala Leu Glu Ile
305                 310                 315                     320

Gln Pro Asp Gln Met Gln Thr Val Asn Ala Ile Leu Ile Val Ile Met
                325                 330                 335

Val Pro Ile Phe Asp Ala Val Leu Tyr Pro Leu Ile Ala Lys Cys Gly
            340                 345                 350

Phe Asn Phe Thr Ser Leu Lys Lys Met Ala Val Gly Met Val Leu Ala
        355                 360                 365

Ser Met Ala Phe Val Val Ala Ala Ile Val Gln Val Glu Ile Asp Lys
    370                 375                 380

Thr Leu Pro Val Phe Pro Lys Gly Asn Glu Val Gln Ile Lys Val Leu
385                 390                 395                     400

Asn Ile Gly Asn Asn Thr Met Asn Ile Ser Leu Pro Gly Glu Met Val
                405                 410                 415

Thr Leu Gly Pro Met Ser Gln Thr Asn Ala Phe Met Thr Phe Asp Val
            420                 425                 430

Asn Lys Leu Thr Arg Ile Asn Ile Ser Ser Pro Gly Ser Pro Val Thr
        435                 440                 445

Ala Val Thr Asp Asp Phe Lys Gln Gly Gln Arg His Thr Leu Leu Val
    450                 455                 460

Trp Ala Pro Asn His Tyr Gln Val Val Lys Asp Gly Leu Asn Gln Lys
465                 470                 475                     480

Pro Glu Lys Gly Glu Asn Gly Ile Arg Phe Val Asn Thr Phe Asn Glu
                485                 490                 495

Leu Ile Thr Ile Thr Met Ser Gly Lys Val Tyr Ala Asn Ile Ser Ser
            500                 505                 510

Tyr Asn Ala Ser Thr Tyr Gln Phe Phe Pro Ser Gly Ile Lys Gly Phe
        515                 520                 525

Thr Ile Ser Ser Thr Glu Ile Pro Pro Gln Cys Gln Pro Asn Phe Asn
    530                 535                 540

Thr Phe Tyr Leu Glu Phe Gly Ser Ala Tyr Thr Tyr Ile Val Gln Arg
545                 550                 555                     560

Lys Asn Asp Ser Cys Pro Glu Val Lys Val Phe Glu Asp Ile Ser Ala
                565                 570                 575

Asn Thr Val Asn Met Ala Leu Gln Ile Pro Gln Tyr Phe Leu Leu Thr
            580                 585                 590

Cys Gly Glu Val Val Phe Ser Val Thr Gly Leu Glu Phe Ser Tyr Ser
        595                 600                 605

Gln Ala Pro Ser Asn Met Lys Ser Val Leu Gln Ala Gly Trp Leu Leu
    610                 615                 620

Thr Val Ala Val Gly Asn Ile Ile Val Leu Ile Val Ala Gly Ala Gly
625                 630                 635                     640

```
Gln Phe Ser Lys Gln Trp Ala Glu Tyr Ile Leu Phe Ala Ala Leu Leu
            645                 650                 655

Leu Val Val Cys Val Ile Phe Ala Ile Met Ala Arg Phe Tyr Thr Tyr
            660                 665                 670

Ile Asn Pro Ala Glu Ile Glu Ala Gln Phe Asp Glu Asp Glu Lys Lys
            675                 680                 685

Asn Arg Leu Glu Lys Ser Asn Pro Tyr Phe Met Ser Gly Ala Asn Ser
    690                 695                 700

Gln Lys Gln Met
705
```

(2) INFORMATION FOR SEQ ID NO:3:

(i) SEQUENCE CHARACTERISTICS:
        (A) LENGTH: 2746 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Oryctolagus cuniculus (ix) FEATURE:
        (A) NAME/KEY: CDS
        (B) LOCATION: 31..2154

(xi) SEQUENCE DESCRIPTION: SEQ ID NO:3:

```
CCACGCGTCC  GAGCCCTAGG  AGCAGCCACC  ATG GGA ATG TCT AAG TCA CTG AGC        54
                                    Met Gly Met Ser Lys Ser Leu Ser
                                     1               5

TGC TTC GGC TAT CCC CTG AGC ATC TTC TTC ATC GTG GTC AAT GAG TTC           102
Cys Phe Gly Tyr Pro Leu Ser Ile Phe Phe Ile Val Val Asn Glu Phe
     10              15                  20

TGC GAA AGG TTC TCC TAC TAT GGG ATG AGA GCA CTC CTG ATT CTG TAC           150
Cys Glu Arg Phe Ser Tyr Tyr Gly Met Arg Ala Leu Leu Ile Leu Tyr
 25              30                  35                      40

TTC AGA AAC TTC ATC GGC TGG GAC GAC AAC CTG TCC ACG GTC ATC TAC           198
Phe Arg Asn Phe Ile Gly Trp Asp Asp Asn Leu Ser Thr Val Ile Tyr
                 45                  50                  55

CAC ACG TTC GTC GCG CTG TGC TAC CTC ACG CCC ATT CTC GGA GCT CTC           246
His Thr Phe Val Ala Leu Cys Tyr Leu Thr Pro Ile Leu Gly Ala Leu
             60                  65                  70

ATC GCC GAC GCG TGG CTG GGG AAG TTC AAG ACC ATC GTG TGG CTG TCC           294
Ile Ala Asp Ala Trp Leu Gly Lys Phe Lys Thr Ile Val Trp Leu Ser
         75                  80                  85

ATC GTC TAC ACC ATC GGA CAA GCA GTC ACC TCC CTC AGC TCC GTC AAT           342
Ile Val Tyr Thr Ile Gly Gln Ala Val Thr Ser Leu Ser Ser Val Asn
     90                  95                 100

GAG CTC ACA GAC AAC AAC CAT GAC GGG ACC CCC GAC AGC CTC CCT GTG           390
Glu Leu Thr Asp Asn Asn His Asp Gly Thr Pro Asp Ser Leu Pro Val
105             110                 115                 120

CAC GTG GCG GTG TGC ATG ATC GGC CTG CTC CTG ATA GCC CTC GGG ACA           438
His Val Ala Val Cys Met Ile Gly Leu Leu Leu Ile Ala Leu Gly Thr
                125                 130                 135

GGA GGA ATC AAG CCC TGT GTG TCT GCC TTT GGC GGC GAT CAG TTT GAG           486
Gly Gly Ile Lys Pro Cys Val Ser Ala Phe Gly Gly Asp Gln Phe Glu
            140                 145                 150

GAG GGC CAG GAA AAG CAA AGA AAC CGG TTT TTT TCC ATC TTT TAC TTG           534
```

|     |     |     |     |     |     |     |     |     |     |     |     |     |     |     |     |
| --- | --- | --- | --- | --- | --- | --- | --- | --- | --- | --- | --- | --- | --- | --- | --- |
| Glu | Gly | Gln | Glu | Lys | Gln | Arg | Asn | Arg | Phe | Phe | Ser | Ile | Phe | Tyr | Leu |
|     |     | 155 |     |     |     | 160 |     |     |     |     | 165 |     |     |     |     |

| GCC | ATT | AAC | GCT | GGG | AGT | CTG | CTG | TCC | ACA | ATC | ATC | ACC | CCC | ATG | GTC | 582 |
| --- | --- | --- | --- | --- | --- | --- | --- | --- | --- | --- | --- | --- | --- | --- | --- | --- |
| Ala | Ile | Asn | Ala | Gly | Ser | Leu | Leu | Ser | Thr | Ile | Ile | Thr | Pro | Met | Val |     |
|     | 170 |     |     |     | 175 |     |     |     |     |     | 180 |     |     |     |     |     |
| AGA | GTT | CAA | CAA | TGT | GGA | ATT | CAC | GTT | AAA | CAA | GCT | TGC | TAC | CCA | CTG | 630 |
| Arg | Val | Gln | Gln | Cys | Gly | Ile | His | Val | Lys | Gln | Ala | Cys | Tyr | Pro | Leu |     |
| 185 |     |     |     |     | 190 |     |     |     |     | 195 |     |     |     |     | 200 |     |
| GCC | TTT | GGG | ATT | CCT | GCT | ATC | CTC | ATG | GCT | GTA | TCC | CTG | ATC | GTG | TTC | 678 |
| Ala | Phe | Gly | Ile | Pro | Ala | Ile | Leu | Met | Ala | Val | Ser | Leu | Ile | Val | Phe |     |
|     |     |     |     | 205 |     |     |     |     | 210 |     |     |     |     | 215 |     |     |
| ATC | ATC | GGC | AGT | GGG | ATG | TAC | AAG | AAG | TTC | AAG | CCG | CAG | GGG | AAC | ATC | 726 |
| Ile | Ile | Gly | Ser | Gly | Met | Tyr | Lys | Lys | Phe | Lys | Pro | Gln | Gly | Asn | Ile |     |
|     |     |     | 220 |     |     |     |     | 225 |     |     |     |     | 230 |     |     |     |
| CTG | AGC | AAA | GTG | GTG | AAG | TGC | ATC | TGC | TTT | GCC | ATC | AAA | AAT | AGG | TTT | 774 |
| Leu | Ser | Lys | Val | Val | Lys | Cys | Ile | Cys | Phe | Ala | Ile | Lys | Asn | Arg | Phe |     |
|     |     | 235 |     |     |     |     | 240 |     |     |     |     | 245 |     |     |     |     |
| AGG | CAC | CGC | AGT | AAG | CAG | TTT | CCC | AAG | AGG | GCG | CAC | TGG | CTG | GAC | TGG | 822 |
| Arg | His | Arg | Ser | Lys | Gln | Phe | Pro | Lys | Arg | Ala | His | Trp | Leu | Asp | Trp |     |
|     | 250 |     |     |     |     | 255 |     |     |     |     | 260 |     |     |     |     |     |
| GCT | AAG | GAG | AAA | TAC | GAC | GAG | CGG | CTT | ATC | GCG | CAG | ATC | AAG | ATG | GTT | 870 |
| Ala | Lys | Glu | Lys | Tyr | Asp | Glu | Arg | Leu | Ile | Ala | Gln | Ile | Lys | Met | Val |     |
| 265 |     |     |     |     | 270 |     |     |     |     | 275 |     |     |     |     | 280 |     |
| ACG | AGG | GTG | CTG | TTC | CTG | TAC | ATC | CCA | CTC | CCC | ATG | TTC | TGG | GCC | TTG | 918 |
| Thr | Arg | Val | Leu | Phe | Leu | Tyr | Ile | Pro | Leu | Pro | Met | Phe | Trp | Ala | Leu |     |
|     |     |     |     | 285 |     |     |     |     | 290 |     |     |     |     | 295 |     |     |
| TTT | GAT | CAG | CAG | GGT | TCC | AGA | TGG | ACG | CTG | CAA | GCG | ACG | ACC | ATG | TCC | 966 |
| Phe | Asp | Gln | Gln | Gly | Ser | Arg | Trp | Thr | Leu | Gln | Ala | Thr | Thr | Met | Ser |     |
|     |     |     | 300 |     |     |     |     | 305 |     |     |     |     | 310 |     |     |     |
| GGG | AGA | ATT | GGA | ATC | CTT | GAA | ATT | CAG | CCG | GAT | CAG | ATG | CAG | ACT | GTG | 1014 |
| Gly | Arg | Ile | Gly | Ile | Leu | Glu | Ile | Gln | Pro | Asp | Gln | Met | Gln | Thr | Val |     |
|     |     | 315 |     |     |     |     | 320 |     |     |     |     | 325 |     |     |     |     |
| AAC | ACC | ATC | TTG | ATT | ATT | ATC | CTG | GTC | CCC | ATC | ATG | GAC | GCC | GTG | GTG | 1062 |
| Asn | Thr | Ile | Leu | Ile | Ile | Ile | Leu | Val | Pro | Ile | Met | Asp | Ala | Val | Val |     |
|     | 330 |     |     |     |     | 335 |     |     |     |     | 340 |     |     |     |     |     |
| TAT | CCT | CTG | ATT | GCA | AAG | TGT | GGC | CTC | AAC | TTC | ACC | TCT | CTG | AAG | AAG | 1110 |
| Tyr | Pro | Leu | Ile | Ala | Lys | Cys | Gly | Leu | Asn | Phe | Thr | Ser | Leu | Lys | Lys |     |
| 345 |     |     |     |     | 350 |     |     |     |     | 355 |     |     |     |     | 360 |     |
| ATG | ACG | ATT | GGG | ATG | TTC | CTG | GCT | TCC | ATG | GCC | TTC | GTG | GCA | GCT | GCA | 1158 |
| Met | Thr | Ile | Gly | Met | Phe | Leu | Ala | Ser | Met | Ala | Phe | Val | Ala | Ala | Ala |     |
|     |     |     |     | 365 |     |     |     |     | 370 |     |     |     |     | 375 |     |     |
| ATC | CTG | CAG | GTG | GAA | ATC | GAT | AAA | ACT | CTT | CCT | GTC | TTC | CCC | AAA | GCC | 1206 |
| Ile | Leu | Gln | Val | Glu | Ile | Asp | Lys | Thr | Leu | Pro | Val | Phe | Pro | Lys | Ala |     |
|     |     |     | 380 |     |     |     |     | 385 |     |     |     |     | 390 |     |     |     |
| AAT | GAA | GTC | CAA | ATT | AAA | GTT | CTG | AAT | GTA | GGA | AGT | GAG | AAC | ATG | ATC | 1254 |
| Asn | Glu | Val | Gln | Ile | Lys | Val | Leu | Asn | Val | Gly | Ser | Glu | Asn | Met | Ile |     |
|     |     | 395 |     |     |     |     | 400 |     |     |     |     | 405 |     |     |     |     |
| ATC | TCT | CTT | CCT | GGG | CAG | ACG | GTG | ACG | CTC | AAC | CAG | ATG | TCT | CAA | ACG | 1302 |
| Ile | Ser | Leu | Pro | Gly | Gln | Thr | Val | Thr | Leu | Asn | Gln | Met | Ser | Gln | Thr |     |
|     | 410 |     |     |     |     | 415 |     |     |     |     | 420 |     |     |     |     |     |
| AAT | GAA | TTC | ATG | ACT | TTC | AAT | GAA | GAC | ACA | CTG | ACA | AGC | ATA | AAC | ATC | 1350 |
| Asn | Glu | Phe | Met | Thr | Phe | Asn | Glu | Asp | Thr | Leu | Thr | Ser | Ile | Asn | Ile |     |
| 425 |     |     |     |     | 430 |     |     |     |     | 435 |     |     |     |     | 440 |     |
| ACT | TCC | GGA | TCA | CAA | GTC | ACC | ATG | ATC | ACA | CCC | AGC | CTT | GAG | GCA | GGC | 1398 |
| Thr | Ser | Gly | Ser | Gln | Val | Thr | Met | Ile | Thr | Pro | Ser | Leu | Glu | Ala | Gly |     |
|     |     |     |     | 445 |     |     |     |     | 450 |     |     |     |     | 455 |     |     |
| CAG | CGC | CAC | ACC | CTG | CTG | GTG | TGG | GCC | CCC | AAT | AAC | TAC | CGA | GTG | GTC | 1446 |
| Gln | Arg | His | Thr | Leu | Leu | Val | Trp | Ala | Pro | Asn | Asn | Tyr | Arg | Val | Val |     |
|     |     |     | 460 |     |     |     |     | 465 |     |     |     |     | 470 |     |     |     |
| AAT | GAC | GGC | CTG | ACC | CAG | AAG | TCA | GAC | AAA | GGA | GAA | AAT | GGA | ATC | AGG | 1494 |

```
Asn Asp Gly Leu Thr Gln Lys Ser Asp Lys Gly Glu Asn Gly Ile Arg
        475                 480                 485

TTT GTG AAC ACT TAC AGC CAG CCC ATC AAC GTC ACG ATG AGC GGG AAA    1542
Phe Val Asn Thr Tyr Ser Gln Pro Ile Asn Val Thr Met Ser Gly Lys
    490                 495                 500

GTT TAC GAA CAC ATC GCC AGC TAC AAT GCC AGC GAG TAT CAG TTT TTC    1590
Val Tyr Glu His Ile Ala Ser Tyr Asn Ala Ser Glu Tyr Gln Phe Phe
505                 510                 515                 520

ACT TCT GGA GTA AAG GGC TTC ACC GTC AGC TCG GCA GGC ATC TCG GAG    1638
Thr Ser Gly Val Lys Gly Phe Thr Val Ser Ser Ala Gly Ile Ser Glu
                525                 530                 535

CAG TGC AGG CGG GAC TTT GAG TCT CCG TAC CTG GAG TTT GGC AGC GCG    1686
Gln Cys Arg Arg Asp Phe Glu Ser Pro Tyr Leu Glu Phe Gly Ser Ala
            540                 545                 550

TAC ACG TAC CTG ATC ACG AGC CAG GCT ACT GGC TGC CCC CAA GTG ACG    1734
Tyr Thr Tyr Leu Ile Thr Ser Gln Ala Thr Gly Cys Pro Gln Val Thr
        555                 560                 565

GAG TTT GAA GAT ATT CCG CCC AAC ACA ATG AAC ATG GCT TGG CAA ATC    1782
Glu Phe Glu Asp Ile Pro Pro Asn Thr Met Asn Met Ala Trp Gln Ile
    570                 575                 580

CCA CAG TAC TTC CTC ATC ACC TCT GGC GAG GTG GTC TTC TCC ATC ACG    1830
Pro Gln Tyr Phe Leu Ile Thr Ser Gly Glu Val Val Phe Ser Ile Thr
585                 590                 595                 600

GGC CTG GAG TTC TCC TAT TCT CAG GCT CCT TCC AAC ATG AAG TCG GTG    1878
Gly Leu Glu Phe Ser Tyr Ser Gln Ala Pro Ser Asn Met Lys Ser Val
                605                 610                 615

CTG CAG GCC GGG TGG CTG CTG ACG GTG GCT GTG GGC AAC ATC ATT GTG    1926
Leu Gln Ala Gly Trp Leu Leu Thr Val Ala Val Gly Asn Ile Ile Val
            620                 625                 630

CTC ATC GTG GCC GGC GCG GGC CAG ATC AAC AAG CAG TGG GCC GAG TAC    1974
Leu Ile Val Ala Gly Ala Gly Gln Ile Asn Lys Gln Trp Ala Glu Tyr
        635                 640                 645

ATC CTC TTT GCC GCC CTG CTC CTG GTC GTC TGT GTC ATA TTT GCC ATC    2022
Ile Leu Phe Ala Ala Leu Leu Leu Val Val Cys Val Ile Phe Ala Ile
    650                 655                 660

ATG GCT CGA TTC TAT ACG TAT GTC AAC CCG GCC GAG ATC GAG GCT CAG    2070
Met Ala Arg Phe Tyr Thr Tyr Val Asn Pro Ala Glu Ile Glu Ala Gln
665                 670                 675                 680

TTT GAA GAA GAT GAG AAG AAA AAG AAC CCA GAA AAG AAC GAC CTC TAC    2118
Phe Glu Glu Asp Glu Lys Lys Lys Asn Pro Glu Lys Asn Asp Leu Tyr
                685                 690                 695

CCC TCG CTG GCG CCC GTC TCA CAG ACA CAG ATG TGAGTCTGGA GGCGGTGTAG  2171
Pro Ser Leu Ala Pro Val Ser Gln Thr Gln Met
            700                 705

GAGGCCCACG CCTGGCGTGC ACTGTGACCT CTGTCCGAGG GCGCAGGACG TACCCCTGGG  2231

CAGCCCCGGA AGGAGGACTT GAGAACTGTG AACCAGACCA CGAAAGCTAT GTTCTGAGCA  2291

GCCAGTGATG AGTCCAAAAC TCTGAAAGAA ATCTTGTTGA AAGTCTTATT TAAAACACAC  2351

ACACACACAC ACACACACAC ACACACTTTT CCAACACTGA CAGCCTACCC ATGTTAACTC  2411

CTTCTCTACC AATGCAAATG CTGTTATTTT GGACTAACTT AATTTTGAAC ACTGTTCTAT  2471

GTTGCTTGTA TTCTAACATC CTTAGGAAAG GCAATGTTAA GAGAGGCAGG AGGCAATGCC  2531

AAAGTTGAAT ATGTAGGTTT CAGAATGGTA TATACCACAT ATTACTTAGT ATTAACTGAA  2591

AACCTCAACT TTGAGGTTTT GTTCTATTTT TTCCACTCCT TACCTCTTTT TAACCTGTGT  2651

ACAACTCAAA AGGACCACTC AGATAAAGGC CAGTAAAGAT TTTTTTTGCC GTTTTGATGA  2711

AATAAAATAA TGTTCCTAAG AAAAAAAAAA AAAAA                            2746
```

(2) INFORMATION FOR SEQ ID NO:4:

(i) SEQUENCE CHARACTERISTICS:
        (A) LENGTH: 707 amino acids
        (B) TYPE: amino acid
        (D) TOPOLOGY: linear (ii) MOLECULE TYPE: protein (xi) SEQUENCE DESCRIPTION: SEQ ID NO:4:

| | | | | | | | | | | | | | | |
|---|---|---|---|---|---|---|---|---|---|---|---|---|---|---|
| Met | Gly | Met | Ser | Lys | Ser | Leu | Ser | Cys | Phe | Gly | Tyr | Pro | Leu | Ser | Ile |
| 1 | | | | 5 | | | | | 10 | | | | | 15 |
| Phe | Phe | Ile | Val | Val | Asn | Glu | Phe | Cys | Glu | Arg | Phe | Ser | Tyr | Tyr | Gly |
| | | | 20 | | | | | 25 | | | | | 30 | |
| Met | Arg | Ala | Leu | Leu | Ile | Leu | Tyr | Phe | Arg | Asn | Phe | Ile | Gly | Trp | Asp |
| | | 35 | | | | | 40 | | | | | 45 | | |
| Asp | Asn | Leu | Ser | Thr | Val | Ile | Tyr | His | Thr | Phe | Val | Ala | Leu | Cys | Tyr |
| | 50 | | | | | 55 | | | | | 60 | | | | |
| Leu | Thr | Pro | Ile | Leu | Gly | Ala | Leu | Ile | Ala | Asp | Ala | Trp | Leu | Gly | Lys |
| 65 | | | | | 70 | | | | | 75 | | | | | 80 |
| Phe | Lys | Thr | Ile | Val | Trp | Leu | Ser | Ile | Val | Tyr | Thr | Ile | Gly | Gln | Ala |
| | | | | 85 | | | | | 90 | | | | | 95 | |
| Val | Thr | Ser | Leu | Ser | Ser | Val | Asn | Glu | Leu | Thr | Asp | Asn | Asn | His | Asp |
| | | | 100 | | | | | 105 | | | | | 110 | | |
| Gly | Thr | Pro | Asp | Ser | Leu | Pro | Val | His | Val | Ala | Val | Cys | Met | Ile | Gly |
| | | 115 | | | | | 120 | | | | | 125 | | | |
| Leu | Leu | Leu | Ile | Ala | Leu | Gly | Thr | Gly | Gly | Ile | Lys | Pro | Cys | Val | Ser |
| | 130 | | | | | 135 | | | | | 140 | | | | |
| Ala | Phe | Gly | Gly | Asp | Gln | Phe | Glu | Glu | Gly | Gln | Glu | Lys | Gln | Arg | Asn |
| 145 | | | | | 150 | | | | | 155 | | | | | 160 |
| Arg | Phe | Phe | Ser | Ile | Phe | Tyr | Leu | Ala | Ile | Asn | Ala | Gly | Ser | Leu | Leu |
| | | | | 165 | | | | | 170 | | | | | 175 | |
| Ser | Thr | Ile | Ile | Thr | Pro | Met | Val | Arg | Val | Gln | Gln | Cys | Gly | Ile | His |
| | | | 180 | | | | | 185 | | | | | 190 | | |
| Val | Lys | Gln | Ala | Cys | Tyr | Pro | Leu | Ala | Phe | Gly | Ile | Pro | Ala | Ile | Leu |
| | | 195 | | | | | 200 | | | | | 205 | | | |
| Met | Ala | Val | Ser | Leu | Ile | Val | Phe | Ile | Ile | Gly | Ser | Gly | Met | Tyr | Lys |
| | 210 | | | | | 215 | | | | | 220 | | | | |
| Lys | Phe | Lys | Pro | Gln | Gly | Asn | Ile | Leu | Ser | Lys | Val | Val | Lys | Cys | Ile |
| 225 | | | | | 230 | | | | | 235 | | | | | 240 |
| Cys | Phe | Ala | Ile | Lys | Asn | Arg | Phe | Arg | His | Arg | Ser | Lys | Gln | Phe | Pro |
| | | | | 245 | | | | | 250 | | | | | 255 | |
| Lys | Arg | Ala | His | Trp | Leu | Asp | Trp | Ala | Lys | Glu | Lys | Tyr | Asp | Glu | Arg |
| | | | 260 | | | | | 265 | | | | | 270 | | |
| Leu | Ile | Ala | Gln | Ile | Lys | Met | Val | Thr | Arg | Val | Leu | Phe | Leu | Tyr | Ile |
| | | 275 | | | | | 280 | | | | | 285 | | | |
| Pro | Leu | Pro | Met | Phe | Trp | Ala | Leu | Phe | Asp | Gln | Gln | Gly | Ser | Arg | Trp |
| | 290 | | | | | 295 | | | | | 300 | | | | |
| Thr | Leu | Gln | Ala | Thr | Thr | Met | Ser | Gly | Arg | Ile | Gly | Ile | Leu | Glu | Ile |
| 305 | | | | | 310 | | | | | 315 | | | | | 320 |
| Gln | Pro | Asp | Gln | Met | Gln | Thr | Val | Asn | Thr | Ile | Leu | Ile | Ile | Ile | Leu |
| | | | | 325 | | | | | 330 | | | | | 335 | |
| Val | Pro | Ile | Met | Asp | Ala | Val | Val | Tyr | Pro | Leu | Ile | Ala | Lys | Cys | Gly |
| | | | 340 | | | | | 345 | | | | | 350 | | |
| Leu | Asn | Phe | Thr | Ser | Leu | Lys | Lys | Met | Thr | Ile | Gly | Met | Phe | Leu | Ala |
| | | 355 | | | | | 360 | | | | | 365 | | | |

```
Ser  Met  Ala  Phe  Val  Ala  Ala  Ile  Leu  Gln  Val  Glu  Ile  Asp  Lys
     370            375                 380
Thr  Leu  Pro  Val  Phe  Pro  Lys  Ala  Asn  Glu  Val  Gln  Ile  Lys  Val  Leu
385                 390                 395                           400
Asn  Val  Gly  Ser  Glu  Asn  Met  Ile  Ile  Ser  Leu  Pro  Gly  Gln  Thr  Val
               405                      410                      415
Thr  Leu  Asn  Gln  Met  Ser  Gln  Thr  Asn  Glu  Phe  Met  Thr  Phe  Asn  Glu
               420                 425                      430
Asp  Thr  Leu  Thr  Ser  Ile  Asn  Ile  Thr  Ser  Gly  Ser  Gln  Val  Thr  Met
          435                      440                      445
Ile  Thr  Pro  Ser  Leu  Glu  Ala  Gly  Gln  Arg  His  Thr  Leu  Leu  Val  Trp
     450                      455                 460
Ala  Pro  Asn  Asn  Tyr  Arg  Val  Val  Asn  Asp  Gly  Leu  Thr  Gln  Lys  Ser
465                      470                 475                           480
Asp  Lys  Gly  Glu  Asn  Gly  Ile  Arg  Phe  Val  Asn  Thr  Tyr  Ser  Gln  Pro
               485                      490                      495
Ile  Asn  Val  Thr  Met  Ser  Gly  Lys  Val  Tyr  Glu  His  Ile  Ala  Ser  Tyr
               500                 505                      510
Asn  Ala  Ser  Glu  Tyr  Gln  Phe  Phe  Thr  Ser  Gly  Val  Lys  Gly  Phe  Thr
          515                      520                      525
Val  Ser  Ser  Ala  Gly  Ile  Ser  Glu  Gln  Cys  Arg  Arg  Asp  Phe  Glu  Ser
     530                      535                 540
Pro  Tyr  Leu  Glu  Phe  Gly  Ser  Ala  Tyr  Thr  Tyr  Leu  Ile  Thr  Ser  Gln
545                      550                 555                           560
Ala  Thr  Gly  Cys  Pro  Gln  Val  Thr  Glu  Phe  Glu  Asp  Ile  Pro  Pro  Asn
               565                      570                      575
Thr  Met  Asn  Met  Ala  Trp  Gln  Ile  Pro  Gln  Tyr  Phe  Leu  Ile  Thr  Ser
               580                 585                      590
Gly  Glu  Val  Val  Phe  Ser  Ile  Thr  Gly  Leu  Glu  Phe  Ser  Tyr  Ser  Gln
          595                      600                      605
Ala  Pro  Ser  Asn  Met  Lys  Ser  Val  Leu  Gln  Ala  Gly  Trp  Leu  Leu  Thr
     610                      615                 620
Val  Ala  Val  Gly  Asn  Ile  Ile  Val  Leu  Ile  Val  Ala  Gly  Ala  Gly  Gln
625                      630                 635                           640
Ile  Asn  Lys  Gln  Trp  Ala  Glu  Tyr  Ile  Leu  Phe  Ala  Ala  Leu  Leu  Leu
               645                      650                      655
Val  Val  Cys  Val  Ile  Phe  Ala  Ile  Met  Ala  Arg  Phe  Tyr  Thr  Tyr  Val
               660                      665                      670
Asn  Pro  Ala  Glu  Ile  Glu  Ala  Gln  Phe  Glu  Glu  Asp  Glu  Lys  Lys  Lys
          675                      680                 685
Asn  Pro  Glu  Lys  Asn  Asp  Leu  Tyr  Pro  Ser  Leu  Ala  Pro  Val  Ser  Gln
     690                      695                 700
Thr  Gln  Met
705
```

COMPOSITIONS CORRESPONDING TO A PROTON-COUPLED PEPTIDE TRANSPORTER AND METHODS OF MAKING AND USING SAME

This application is a file wrapper continuation of Ser. No. 08/208,645 filed on Mar. 9, 1994 now abandoned.

This invention was made with U.S. Government support under Grant No. (NIH) DK43171 and (NIH) DK28389 awarded by the National Center for Genomic Research. The U.S. Government has certain rights to this invention.

BACKGROUND OF THE INVENTION

An intestinal peptide-proton cotransporter has been reportedly expressed in *Xenopus laevis* oocytes sites by microinjection of poly A mRNA prepared from rabbit intestinal mucosal cells. This intestinal proton peptide cotransporter has been linked to the transport of dipeptides and oligopeptides and compositions resembling dipeptides and oligopeptides across cell membranes. Such compositions which resemble dipeptides and oligopeptides include β-lactam antibiotics such as the penicillins and cephalosporins. However, attempts to clone and isolate the intestinal peptide-proton cotransporter have been unsuccessful. Attempts to further characterize the cotransporter, such that features of the cotransporter can be used to effect therapy and diagnostics have been limited.

SUMMARY OF THE INVENTION

The present invention features compositions of matter directed to a proton coupled peptide transporter and methods of making and using such proton-coupled peptide transporter. One embodiment of the present invention comprises, as a composition of matter, a non-naturally occurring proton-coupled peptide transporter.

As used herein, the term "non-naturally occurring", in reference to a cell, refers to a cell that has a non-naturally occurring nucleic acid or a non-naturally occurring peptide or is fused to a cell to which it is not fused with in nature. The term "non-naturally occurring nucleic acid" refers to a portion of genomic nucleic acid, cDNA, semi-synthetic nucleic acid, or a synthetic origin nucleic acid which, by virtue of its origin or manipulation is not associated with all the nucleic acid with which it is associated in nature, or is linked to a nucleic acid or other chemical agent other than that to which it is linked in nature, or is not present in nature. The term "a non-naturally occurring peptide" refers to a portion of a large naturally occurring peptide or protein, or semi-synthetic or synthetic peptide, which by virtue of its orgin or manipulation is not associated with all of a peptide with which it is associated in nature, or is linked to peptides, functional groups or chemical agents other than that to which it is linked in nature, or is present in a purity that is not present in nature, or does not occur in nature.

The term "proton" refers to a hydrogen ion and the term "transporter" refers to a composition that participates in the movement of a substrate across the cellular membranes. The present invention is directed a peptide transporter. The proton-coupled peptide transporter transports peptides across cellular membranes, which transport is linked or coupled to the transport of a proton or hydrogen ion across the same membrane.

Preferably, the transporter is a protein corresponding to a nucleic acid sequence within Seq. I.D. Nos. 1 or 3. The term "corresponding" means homologous to or complementary to a particular sequence of nucleic acid. As between nucleic acids and peptides, corresponding refers to amino acids of a peptide in an order derived from the sequence of a nucleic acid or the complement of the nucleic acid. The nucleic acid represented by Seq. I.D. No. 1 is derived from human sources. The nucleic acid of Seq. I.D. No. 3 is derived from rabbit. With respect to Seq. I.D. No. 1, the nucleotides coding the proton-coupled peptide transporter are 57 to 2182. With respect to Seq. I.D. No. 3, the nucleotides coding the proton-coupled peptide transporter are 31 to 2151.

One embodiment of the present invention is directed to a transporter having an amino acid sequence corresponding to the conserved regions of Seq. I.D. Nos. 2 or 4. Preferably, the transporter is a protein having amino acid sequence corresponding substantially to Seq. I.D. Nos. 2 or 4. The term "substantially", in this context, refers to a peptide which may comprise substitutions and modifications which do not alter the activity of the protein to transport peptides across cellular membranes.

The peptide represented by Seq. I.D. No. 2 is derived from human sources. The peptide represented by Seq. I.D. No. 4 is derived from rabbit.

The transporter is preferably electrogenic. The transporter is active in transporting proteins across membranes independent of extra cellular sodium, potassium and chloride ions and independent of membrane potential at pH approximately at 5.5 but dependent on membrane potential at approximately 7.4. The transporter of the present invention is particularly useful in transporting dipeptides across cellular membranes. A preferred dipeptide is the dipeptide, glycyl-sarcosine (Gly-Sar).

One further composition of the present invention features a non-naturally occurring nucleic acid encoding a proton coupled peptide transporter. Preferably, the nucleic acid has a nucleotide sequence corresponding to the conserved regions of Seq. I.D. Nos. 1 and 3.

One embodiment of the present invention features a nucleic acid which corresponds substantially to Seq. I.D. Nos. 1 or 3. As used in this context, the term "substantially" refers to nucleic acid substitutions which do not alter the encoding of the amino acid or encode for such amino acids which do not alter the function of the protein to which it encodes in transporting peptides across cellular membranes.

A further embodiment of the present invention features a method of transporting a chemical across a cellular membrane having a proton-coupled peptide transporter. The method comprises the steps of coupling the chemical to a peptide transported by the proton coupled peptide transporter to form a peptide coupled chemical. The peptide coupled chemical is applied to the cellular membrane to allow the proton coupled peptide transporter to transport the chemical with the peptide. The proton-coupled peptide transporter is capable of transporting any dipeptide or tripeptide. Preferred peptides are alanyl-aspartate, glycyl-leucine or glycyl-sarcosine.

The cellular membrane can be a component of the gastrointestinal tract, the brain, the blood brain barrier, kidney or liver. In the kidney, the proton-coupled peptide transporter is expressed in the kidney proximal tubules. In the liver the proton-coupled peptide transporter is strongly expressed by hepatocytes. In the brain, the proton-coupled peptide transporter is expressed in glial cells or neurons.

One embodiment of the present invention is directed to the transport of a desired composition across a cellular membrane of the gastro-intestinal tract. The method comprises the step of linking the desired chemical to a peptide. The chemical and peptide are transported across the cellular membrane in a constant, steady state manner by a proton-coupled peptide transporter.

One embodiment of the present invention directed to the transport of a desired chemical across the blood brain barrier. The method comprises the step of linking the desired chemical to a peptide capable of being transported across the cellular membranes by a proton-coupled peptide transporter. The chemical and peptide are transported across the blood brain barrier by a proton-coupled peptide transporter. Embodiments of the present invention allow a chemical which is not normally transported to the brain to enter the brain by active transport.

A further embodiment of the present invention features a method of identifying chemicals capable of interacting with a proton-coupled peptide transporter. The method comprises the steps of applying one or more chemicals to one or more cells having a non-naturally occurring nucleic acid coding a proton-coupled peptide transporter operably linked to a promoter. Upon imposition of conditions for expression of such nucleic acid, the cell makes the proton-coupled peptide transporter. The cell is monitored for the uptake of peptides which uptake in the presence of the chemical in amounts greater than when the cell is free of the chemical is indicative of agonist activity and which uptake is less in the absence of the chemical is indicative of inhibitory action.

As used herein, the term "apply" refers to placing in contact as in immersing, wetting, or dowsing with a solution containing a material.

The cell may be monitored for the uptake of the chemical by measuring the presence of the chemical in the cell or by monitoring substrate evoked current.

A further embodiment of the present invention features a method of blocking or inhibiting the uptake of peptides by a cell having a proton-coupled peptide transporter. The method comprises the steps of placing a first nucleic acid capable of binding to a second nucleic acid coding the proton-coupled peptide transporter to block expression of such second nucleic acid.

These and other features will become apparent from the drawings, detailed discussion, and examples which follow which, by way of example, without limitation, describe preferred embodiments of the present invention.

BRIEF DESCRIPTION OF THE DRAWINGS

FIG. 1A and B depicts the nucleic acid sequence of a proton-coupled peptide transporter embodying features of the present invention derived from humans, which nucleic acid sequence is presented in SEQ. ID. NO: 1;

FIG. 2 depicts an amino acid sequence of a proton-coupled peptide transporter embodying features of the present invention derived from humans, which sequence is also presented as SEQ. ID. NO: 2;

FIG. 3A, and 3B depict the nucleic acid sequence of a proton-coupled peptide transporter embodying features of the present invention derived from rabbit, which nucleic acid sequence is presented in SEQ. ID. NO: 3;

FIG. 4 depicts an amino acid sequence of a proton-coupled peptide transporter embodying features of the present invention derived from rabbit, which sequence is also presented as SEQ. ID. NO: 4;

DETAILED DESCRIPTION

The present invention will be described in detail as compositions corresponding to a proton-coupled peptide transporter and methods of making and using the same. The sequences presented herein are derived from mammals, and in particular from rabbit and human sources. The sequences derived from rabbit and human sources are anticipated to correspond closely to nucleic acid coding a proton-coupled peptide transporter derived from other species.

Turning now to FIG. 1a and b, a nucleic acid having a nucleotide sequence coding a proton-coupled peptide transporter derived from human sources is depicted. This nucleic acid is presented as Seq. I.D. No. 1. The nucleic acid has 2251 nucleotides and codes a protein having 708 amino acids from nucleotides 57 to 2182. This protein is depicted in FIG. 2 and is presented as Seq. I.D. No. 2.

Turning now to FIG. 3a–3c, a nucleic acid having a nucleotide sequence coding a protein-coupled peptide transporter derived from rabbit is depicted. This nucleic acid is presented as Seq. I.D. No. 3. This nucleic acid has 2746 nucleotides and codes a protein having 707 amino acids from nucleotides 31 to 2151. This protein is depicted in FIG. 4 and is presented as Seq. I.D. No. 4.

Figure 5:
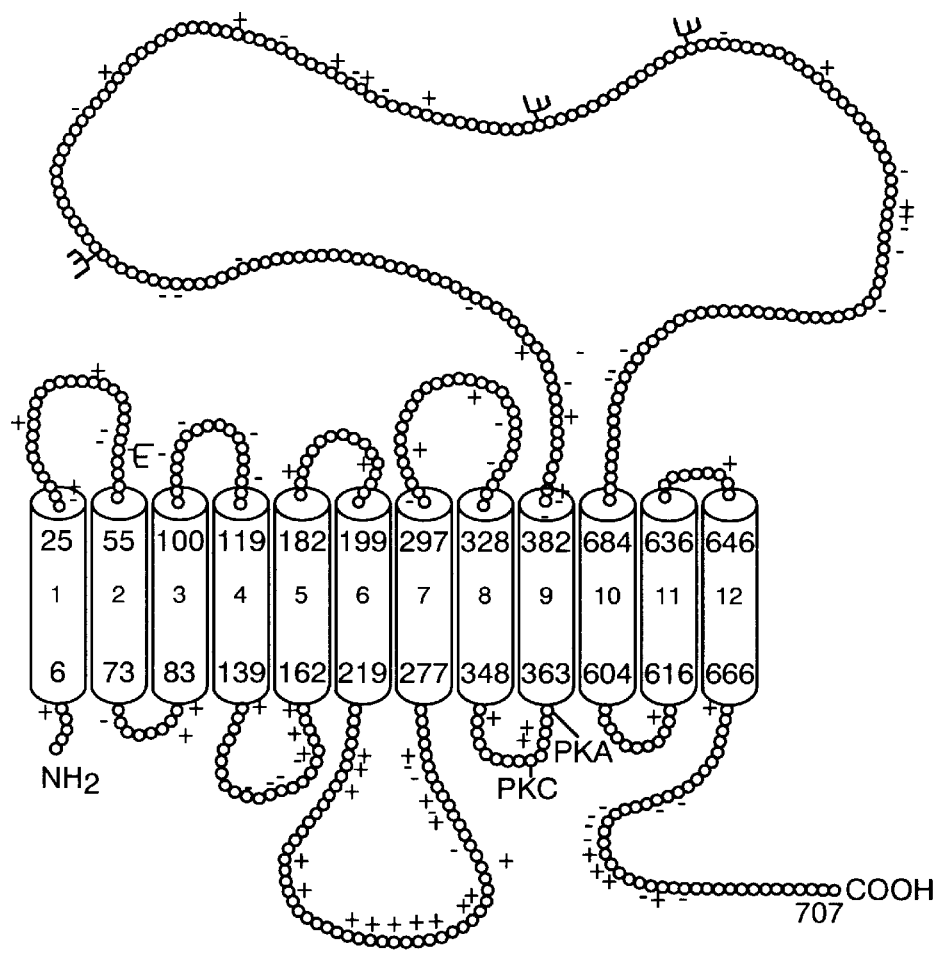
FIG. 5 schematically depicts a proton-coupled peptide transporter with twelve membrane spanning regions.

FIG. 5 depicts a schematic representation of the protein based on the amino acid sequence, with twelve membrane spanning regions. The protein features a large hydrophilic loop which represents a possible target for N-linked glycosylation and is predicted to be extracellular.

The proton-coupled peptide transporter displays broad substrate specificity. The transport of peptides by this protein is electrogenic, independent of extracellular sodium, potassium and chloride ion concentration and independent of membrane potential at pH 5.5 but dependent on membrane potential at pH 7.5.

Messenger RNA coding the proton-coupled peptide transporter is found in the intestine, kidney, liver, and, at a low level, in the brain. In the intestine, the proton-coupled peptide transporter constitutes a major mechanism for the absorption of products of protein digestion and mediates the absorption of compositions with structural similarities to peptides such as β-lactam antibiotics. In the kidney, the proton-coupled peptide transporter absorbs and transports filtered peptides, peptide-derived antibiotics and peptides produced by reaction of luminal peptides. In the liver, the proton-coupled peptide transporter is expected to remove the degradation products of peptide hormones and peptide derived drugs from the circulation. In the brain, the proton-coupled peptide transporter is expected to clear degraded neurotransmitters and facilitates the movement of peptides across the blood-brain barrier.

The transport of peptides across cellular membranes by this protein is electrogenic. Large inward currents are obtained when substrates such as dipeptides, tripeptides, and β-lactam antibiotics are applied to membranes having the transporter. Moreover, single amino acids and peptides containing more than four amino acids do not evoke a current. Transport of oligopeptides was saturable with $K_m$ values ranging between 137 μM and 4.2 mM. The $K_m$ for Gly-Sar is 1.9 mM.

The proton-coupled peptide transporter exhibited a preference for the transport of dimers. Oligopeptides are transported by the proton-coupled peptide transporter, regardless of whether they contained acidic, basic, or hydrophobic amino acids. Any dipeptide can serve as a substrate for proton-coupled peptide transporter. The affinities among dipeptides, however, varied substantially. The proton-coupled peptide transporter appears to have a preference for peptides containing bulky aliphatic side-chains. A large inward current was evoked by the acidic dipeptide Ala-Asp. This may indicate that the β-carboxyl group of aspartic acid is transported in protonated form.

Significant currents were also observed for amino-cephalosporins such as cephalexin, cephradine and cefadroxil. PepT1 displayed a much higher affinity for cyclacillin ($K_m$=137 μM) than for cephalexin ($K_m$=4.2 μM).

Uptake mediated by the proton-coupled peptide transporter is independent of extracellular sodium and chloride ions, and is not coupled to the countertransport of potassium. Transport by the proton-coupled peptide transporter in oocytes was maximal at an extracellular pH ($pH_o$) of 5.5.

Hydrogen ion cotransport was directly demonstrated by measuring intracellular pH ($pH_i$) of oocytes using a pH-sensitive micro-electrode filled with a hydrogen selective ionophore. Transport of glycyl-sarcosine not only requires a low $pH_o$ but also causes a decrease in pH. This demonstrates that the peptide transporter described herein cotransports dipeptides and protons.

Anti-sense

Nucleic acid isolated or synthesized in accordance with the sequences described herein have utility as anti-sense genes to prevent the expression of proton-coupled peptide transporter.

Nucleic acid corresponding to the proton-coupled peptide is loaded into a suitable carrier such as a liposome for introduction into a cell. A nucleic acid having eight or more nucleotides is capable of binding to genomic nucleic acid or messenger RNA. Preferably, the anti-sense nucleic acid is comprised of 30 or more nucleotides to provide necessary stability of a hybridization product of genomic nucleic acid or messenger RNA. Methods for loading anti-sense nucleic acid are known in the art as exemplified by U.S. Pat. No. 4,241,046 issued Dec. 23, 1980 to Papahadjopoulos et al.

Peptide Synthesis

Nucleic acid isolated or synthesized in accordance with the sequences described herein have utility to generate peptides. Nucleic acid exemplified by Sequence I.D. Nos. 1 or 3 can be cloned into suitable vectors or used to isolate nucleic acid. The isolated nucleic acid is combined with suitable DNA linkers and promoters and cloned into a suitable vector. The vector can be used to transform a suitable host organisms such as *E. coli* and the peptide coded by the sequences isolated.

Molecular cloning techniques are described in the text *Molecular Cloning: A Laboratory Manual*, Sambrook et al., Coldspring Harbor Laboratory (1989).

Pharmaceutical articles of the present invention are manufactured in a way which is itself well known in the art. For example, the pharmaceutical preparations may be made by means of conventional mixing, granulating, dragee-making, dissolving, or lyophilizing processes. The process to be used will depend ultimately on the physical properties of the active ingredient used.

Suitable excipients are, in particular, fillers such as sugars, for example, lactose or sucrose, mannitol or sorbitol, cellulose preparations and/or calcium, phosphates, or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl-starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate, and/or polyethylene glycol. Dragee cores may be provided with suitable coating which, if desired, may be resistant to gastric juices. For this purpose, concentrated sugar solutions may be used, which may optionally contain gum arabic, talc, polyvinyl-pyrrolidone, polyethylene glycol, and/or titanium dioxide, lacquer solutions, and suitable organic solvents or solvent mixtures. In order to produce coatings resistant to gastric juices, solutions of suitable cellulose preparations such as acetyl-cellulose phthalate or hydroxypropylmethylcellulose phthalate, are used. Dyestuffs and pigments may be added to the tablets of dragee coatings, for example, for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added.

Possible pharmaceutical preparations which can be used rectally include, for example, suppositories, which consist of a combination of the active compounds with a suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyloleate or triglycerides. Aqueous injection suspensions may contain substances which increase the viscosity of the suspension, for example, sodium carboxymethyl cellulose, sorbitol, and/or dextran. Optionally, the suspension may also contain stabilizers.

Additionally, the compounds of the present invention may also be administered encapsulated in liposomes, pharmaceutical compositions wherein the active ingredient is contained either dispersed or variously present in corpuscles consisting of aqueous concentric layers adherent to lipidic layers. The active ingredient, depending upon its solubility, may be present both in the aqueous layer and in the lipidic layer, or in what is generally termed a liposomic suspension. The hydrophobic layer, generally but not exclusively, comprises phospholipids such as lecithin and sphingomycelin, steroids such as cholesterol, more or less ionic surfactants such as dicetylphosphate, stearylamine, or phosphatidic acid, and/or other materials of a hydrophobic nature. The diameters of the liposomes generally range from about 15 nm to 5 microns.

Features of the present invention are further highlighted in the Examples which follow:

EXAMPLE 1

RNA was extracted from jejunum mucosal scrapes of female rabbits (New Zealand White) by the guanidinium isothiocyanate method using cesium-trifluoroacetic acid (Pharmacia). Poly(A)$^+$ RNA was isolated and injected into collagenase-treated and manually-defolliculated *Xenopus laevis* oocytes. Size-fractionation of rabbit jejunum poly (A)$^+$ RNA using preparative gel electrophoresis was performed in accordance with Hediger, U.S. Pat. No. 4,479,861. Size-fractionation of rabbit jejunum poly(A)$^+$ RNA using preparative gel electrophoresis and injection of fractions into oocytes showed peak stimulation of glutamate uptake by an RNA in the size-range of 2.4–4.4 kb.

A directional cDNA library was constructed from this size-range using the SuperScript Plasmid system (GibcoBRL, Md.). cDNA was again size-fractionated using an electrophoresis apparatus described in Hediger, U.S. Pat. No. 4,479,861 to further purify the cDNA to the 2.4–4.4 kb size range, to remove partial cDNA synthesis products, less than 2.4 kb and cDNA polymerization products, greater than 4.4 kb. cDNA, sized to 2.4–4.4 kb was ligated into the NotI and SalI sites of the expression vector pSPORT 1 (GibcoBRL) and electroporated into ElectroMax DH10B cells (GibccBRL).

Plasmid DNA was in vitro transcribed from pools of 300–400 clones and the resulting cRNA injected into oocytes. A pool was identified which induced the uptake of glutamate 12-fold greater than water-injected controls. This pool was sequentially subdivided and in vitro transcribed until a single preferred clone was identified. The preferred clone was able to express a proton-coupled peptide transporter.

This cDNA was sequenced and also used as probes to identify the human nucleic acid coding a proton-coupled peptide transporter. The human nucleic acid was sequenced.

EXAMPLE 2

This example describes the uptake of radiolabeled glycyl-sarcosine ($C^{14}$-Gly-Sar) by *Xenopus laevis* oocytes injected with poly(A)$^+$ RNA from rabbit jejunum or with cRNA synthesized by in vitro transcription of proton-coupled peptide transporter cDNA.

All uptakes in this and the following figures were performed with 6–8 oocytes, 3 days after injection. RNA-injected oocytes were injected with 25 ng cRNA in 50 nl.

Oocytes injected with cRNA coding a proton-coupled peptide transporter were incubated for 1 hour in uptake solution (100 mM NaCl, 2 mM KCl 1 mM MgCl$_2$, 1 mM CaCl$_2$, 3 mM HEPES, 3 mM MES, 3 mM Tris, pH 5.5) in the presence of 100 µM $C^{14}$-glycol-sarcosine (specific radioactivity, 112 mCi/mmol, custom synthesized by the Radiochemical Center, Amersham, U.K.). The oocytes were rinsed with ice-cold washing solution (uptake solution with pH adjusted to 7.5 with Tris base) and the radioactivity of each oocyte was measured by scintillation counting.

Figure 6:
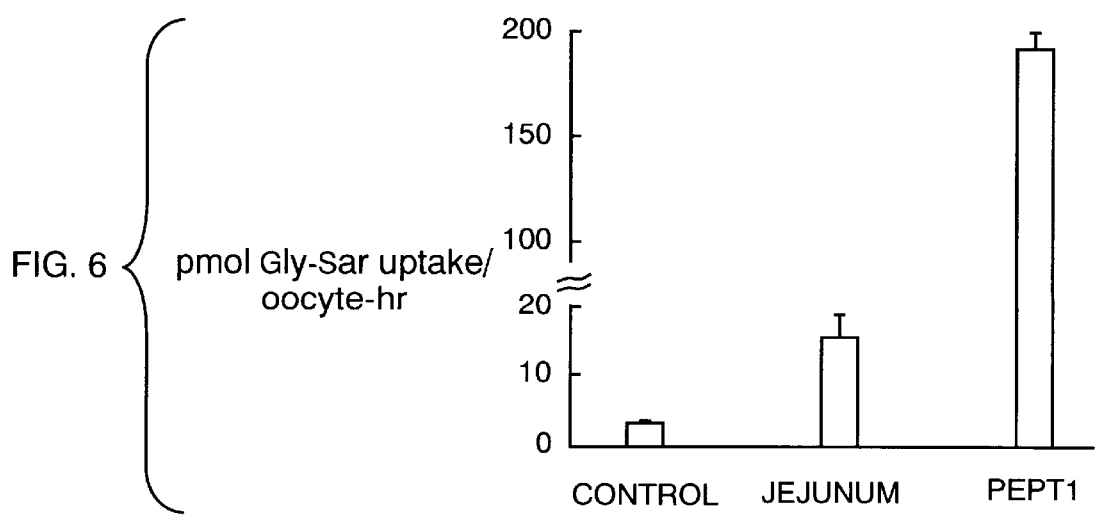
FIG. 6 depicts, in bar graph form, the uptake of carbon 14 labelled glycyl-sarcosine by *Xenopus laevis* oocytes injected with poly A RNA from rabbit intestine or with cRNA synthesized by the transcription of cDNA encoding a proton-coupled peptide transporter of the present invention.

These data is depicted in bar graph form in FIG. 6. Control oocytes, which received no cRNA, are depicted with a solid white bar. The controls exhibited less than 5 pmol uptake of glycyl-sarcosine. Oocytes receiving poly (A)$^+$ RNA exhibited less than 20 pmole uptake of glycyl-sarcosine. Data representing such oocytes is represented by a latched bar in FIG. 6. Oocytes receiving cRNA for a proton-coupled peptide transporter exhibited almost a 200 pmol uptake of glycyl-sarcosine. This data is represented by a solid black bar in FIG. 6. The data suggests that cRNA injected oocytes are capable of actively transporting a peptide, glycyl-sarcosine, across cellular membranes.

EXAMPLE 3

This example describes hybrid depletion of rabbit small intestine poly(A)$^+$ RNA before injection into *Xenopus laevis* oocytes. A first admixture was formed of rabbit small intestine derived poly(A)$^+$ RNA and an antisense DNA oligonucleotide corresponding to the 5'-end coding region of cDNA corresponding to the proton-coupled peptide transporter.

A second admixture was formed of rabbit small intestine derived poly(A)$^+$ RNA and a sense DNA oligonucleotide corresponding to the same region as the antisense DNA. Both DNAs were twenty-three nucleotides in length. Rabbit jejunum poly(A)$^+$ RNA (0.5 µg/µl) was incubated with the oligonucleotide (0.25 µg/µl in the presence of 50 mM NaCl at 42° C. for one hour and then injected into oocytes. The uptake of the peptide, glycyl-sarcosine, was measured three days after injection.

Figure 7:
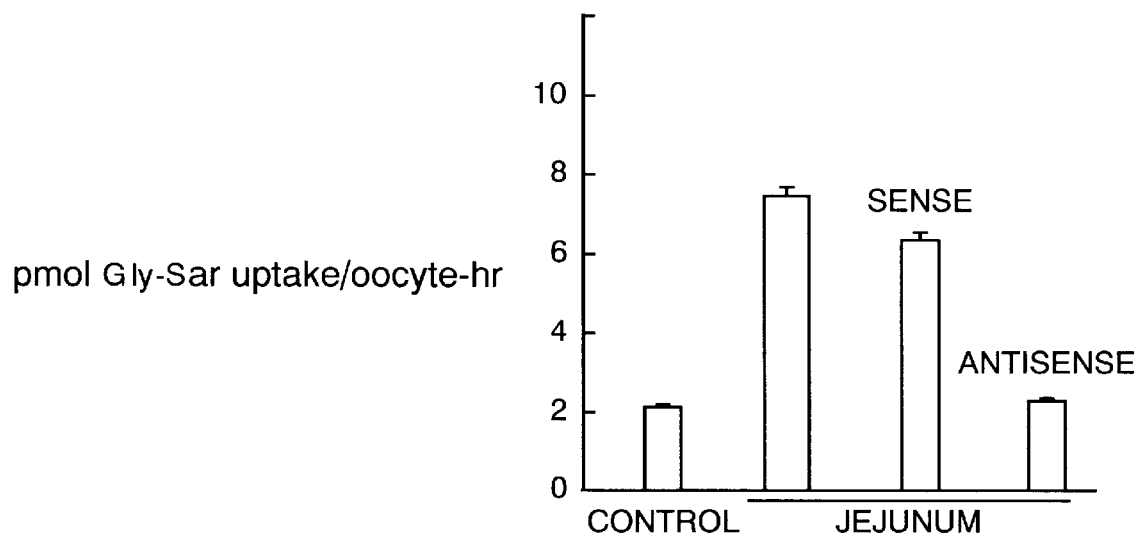
FIG. 7 depicts glycyl-sarcosine uptake by *Xenopus laevis* oocytes following injection with rabbit intestine poly A RNA which was preincubated prior to injection with antisense and sense nucleic acid corresponding to the 5' coding region of cDNA coding the proton-coupled peptide transporter of the present invention.

These data is depicted in bar graph form in FIG. 7. Control oocytes receiving no rabbit intestine poly(A)$^+$ RNA exhibited an uptake of approximately 2 pmol glycyl-sarcosine. This data is represented by a solid white bar in FIG. 7.

Oocytes receiving rabbit poly(A)$^+$ RNA without any sense or antisense nucleic acid exhibited an uptake of approximately 8 pmol glycyl-sarcosine. These data is represented by a first hatched bar, moving from left to right in FIG. 7.

Oocytes receiving sense nucleic acid exhibited approximately 7 pmol glycyl-sarcosine. These data is represented by a second, middle, hatched bar in FIG. 7.

Oocytes receiving antisense nucleic acid exhibited approximately 2 pmol uptake of glycyl-sarcosine. These data is represented by a third hatched bar, to the far right, in FIG. 7.

The data suggests that the antisense DNA suppressed the uptake of the peptide, glycyl-sarcosine, whereas the uptake of the peptide, glycyl-sarcosine, was unaffected by the presence of the sense DNA.

EXAMPLE 4

This example describes the uptake specificity of the proton-coupled peptide transporter. *Xenopus laevis* oocytes were injected with cRNA coding the proton-coupled peptide transporter. These oocytes were subjected to two electrode voltages clamp analysis (Gene Clamp 500, Axon Instruments, California) in the manner described in Kanaisy & Hediger, M. A. *Nature* 360, 467–71 (1992). Readings were made 3–6 days after injection by perfusing the recording chamber with uptake solutions at pH 5.5 containing one of the following compositions, glycyl-sarcosine, glycine, diglycine, triglycine, tetraglycine, pentaglycine, glycyl-leucine, alanine-asparagine, alanyl-lysine, diphenylalanine, tyrosyl-glycine, dileucine, phenylalanyl-leucine, carnosine, methionylphenylalanyl methionine, alanylleucylalanine, caphradine, cefradroxil and cyclacillin.

Figure 8:
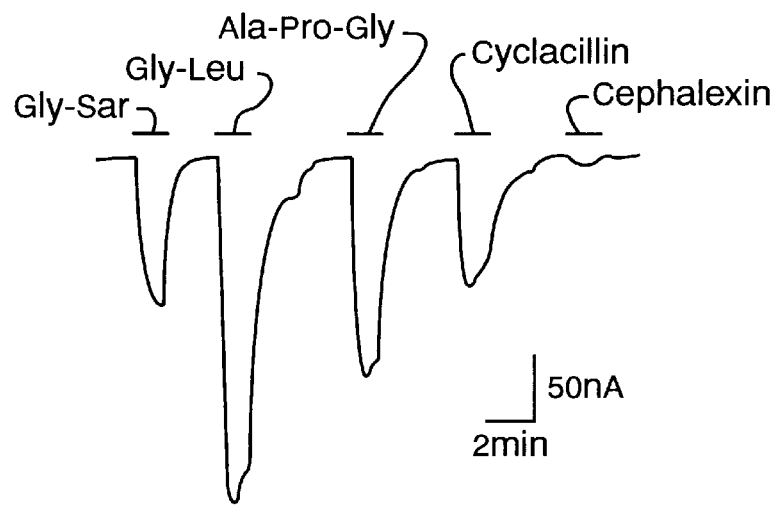
FIG. 8 depicts current responses of *Xenopus laevis* oocytes having cRNA for a proton-coupled peptide transporter following application of different peptides, antibiotics and compound with structural similarities to peptides.
Figure 9:
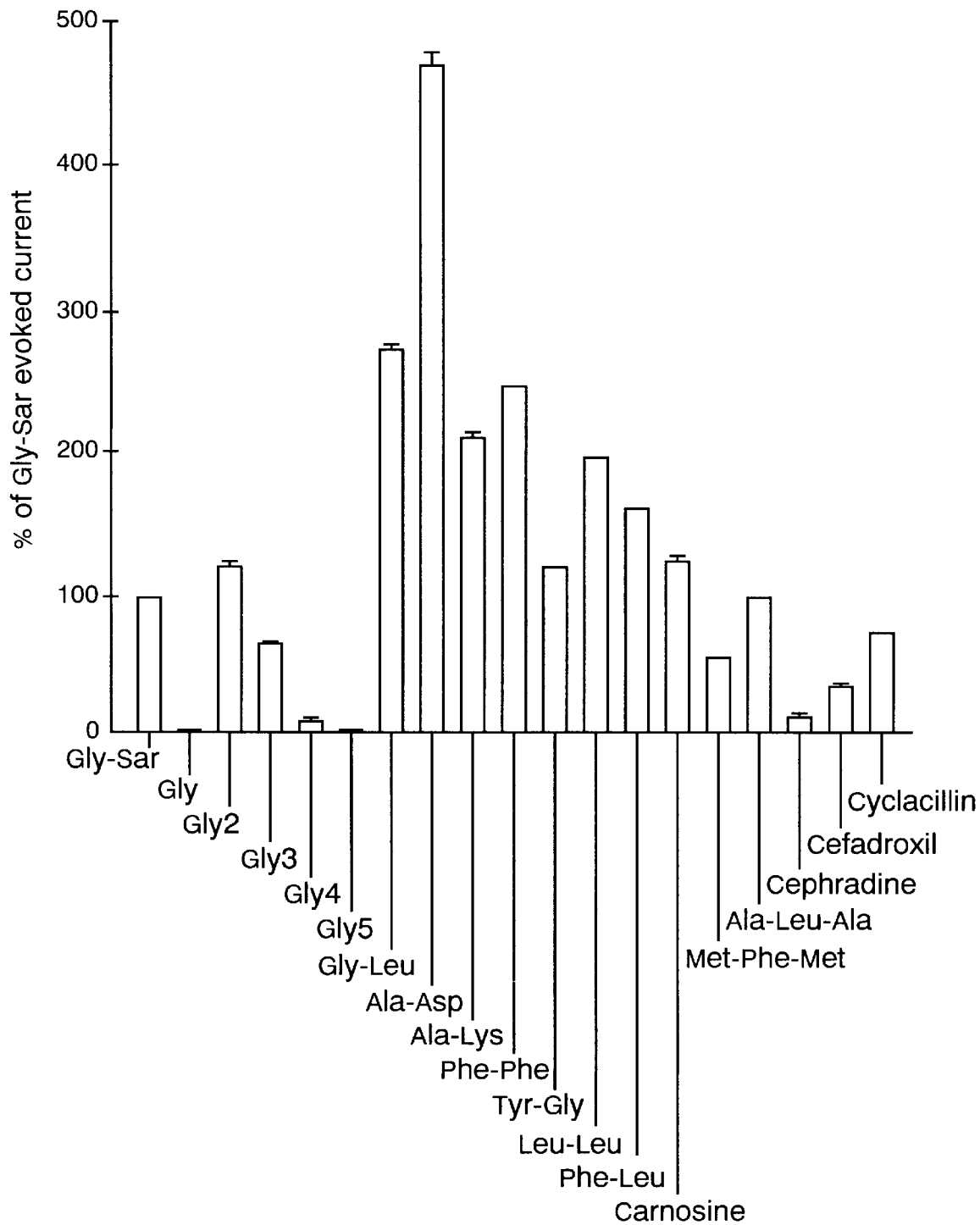
FIG. 9 depicts, in bar graph form, current responses of *Xenopus laevis* oocytes transformed with cRNA for a proton-coupled peptide transporter following an application of a glycyl-sarcosine.

FIG. 8 depicts electrophysiological measurements transformed oocytes in the presense of glycyl-sarcosine, glycyl-leucine, alanylprolinyl-glycine, cycacillin and cephalexin. Each composition is associated with an inward current (inward movement of positive charge). The strongest current is associated with glycyl-sarcosine. The weakest current is associated with cephalexin. FIG. 9 depicts electrophysiological measurements of transformed cocytes as a percent of glycyl-sarcosine evoked current. Data representing glycyl-sarcosine are depicted as a solid black bar. Data representing peptide are depicted with dotted bars. Data representing antibiotics are depicted with hatched bars.

These suggest that the proton-coupled peptide transporter exhibits a preference for alaninyl-aspartate and glycyl-leucine. These data suggest that the transporter exhibits a preference for peptides in the following order: dipeptides, tripeptides, tetrapeptides, and pentapeptides. By altering peptide concentrations, current amplitudes for different compositions, $K_m$ values were determined. These values are set forth in Table I below:

TABLE I

| Glycyl-sarcosine | 1.9 mM |
| Diglycine | 2.5 mM |
| Triglycine | 5.1 mM |
| Glycyl-leucine | 81 $\mu$M |
| Alanyl-aspartate | 143 $\mu$M |
| Cyclacillin | 137 $\mu$M |
| Cephalexin | 4.2 mM |

EXAMPLE 5

This example describes the stoichiometry and voltage dependence of the proton-coupled peptide transporter. Four days after transformation with cRNA coding the proton-coupled peptide transporter, *Xenopus laevis* oocytes were examined in the presence of 1 mMC$^{14}$-glycyl-sarcosine in standard uptake solution (pH 5.5), modified to be sodium or chloride ion free.

In sodium-free solutions, the sodium chloride was replaced with choline-chloride. In chloride free solutions, the sodium chloride was replaced with sodium nitrate.

Figure 10:
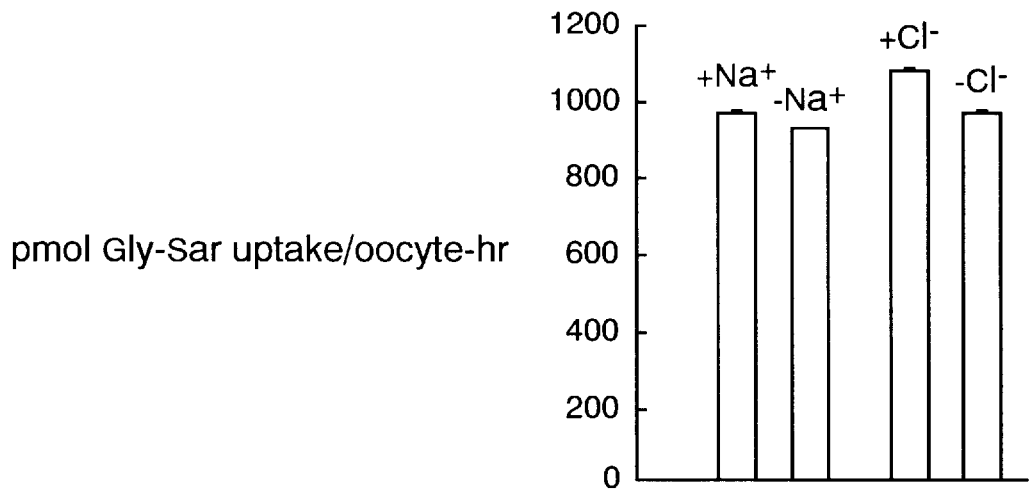
FIG. 10 depicts graphically the uptake of glycyl-sarcosine dipeptides in *Xenopus laevis* oocytes transformed with cRNA for a proton-coupled peptide transporter in the presence of different concentrations of sodium and chloride ions.

Glycyl-sarcosine uptake was determined from the slope of the time-dependence of 1 to 5 minutes uptake. The results are depicted in bar graph form in FIG. 10. These data demonstrate that the proton-coupled peptide transporter transports peptides across cellular membranes independent of sodium concentrations and independent of chloride concentration. That is, the presence of or absence of sodium ion and the presence or absence of chloridion had little or no effect on glycyl-sarcosine uptake. In each instance the uptake was approximately 1000 pmol glycyl-sarcosine.

EXAMPLE 6

In this example *Xenopus laevis* oocytes transformed with cRNA coding the proton-coupled peptide transporter of the preceding example were evaluated for $C^{14}$-glycyl-sarcosine uptake in the standard uptake solutions modified to different pH. Glycyl-sarcosine uptake was determined from the slope of time-dependence of 1 to 5 minute uptakes.

Figure 11:
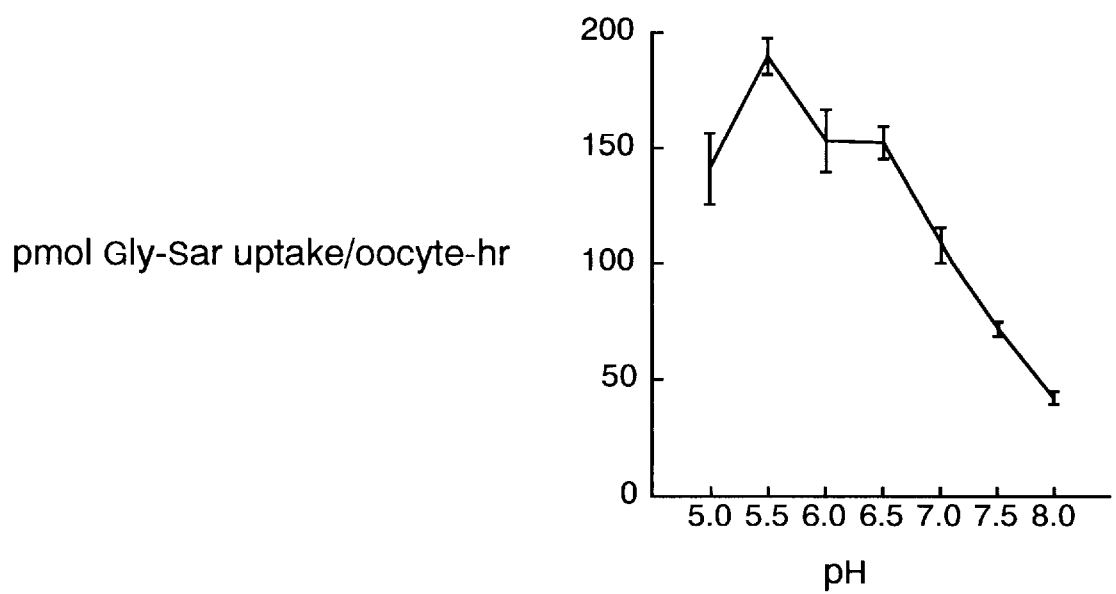
FIG. 11 depicts the uptake of glycyl-sarcosine in *Xenopus laevis* oocytes transformed with cRNA for a proton-coupled peptide transporter in the presence of different concentrations of hydrogen ion.

These data are depicted graphically in FIG. 11. The data suggest a maximum uptake at pH 5.5, with the uptake decreasing at pHs lower than 5.5, and decreasing at pH greater than 5.5. These data suggest a plateau at approximately pH 6 to 6.5.

EXAMPLE 7

The example describes hydrogen ion cotransport by *Xenopus laevis* oocytes transformed with cRNA coding a proton-coupled peptide transporter. Transformed *Xenopus laevis* oocytes of Example 5 and 6 were implanted with microelectrodes and membrane potential set with electrodes. The microelectrodes were filled with 3M KCl and exhibited resistances of 1–10 MOhms.

Internal pH measurements were taken with microelectrodes, silanized borosilicate pipettes with tips filled with a hydrogen ionophore (I-cocktail B, Fluka). The membrane potential was measured in uptake solution (pH 5.5) containing 1 mM glycyl-sarcosine. After washing with uptake solution without glycyl-sarcosine, each oocyte was clamped at this membrane potential. Inward currents evoked by bath-applied 1 mM glycyl-sarcosine at the above determined holding potentials were recorded and the values were converted into the rate of net charge flux using Faraday's constant ($9.65 \times 10^4$ c/mol). The equation used to calculate the electrochemical potential difference for H$^+$ ($\Delta\mu_H$) was $\Delta\mu_H = RT \ln([H^+]_i/[H^+]_o) + zF(V_i - V_o)$ and that for Gly-Sar ($\Delta\mu_{Gly-Sar}$) was $\Delta\mu_{Gly-Sar} = RT \ln([Gly-Sar]_i/[Gly-Sar]_o)$, where; R is the gas constant, T the absolute temperature (295° K.), F is Faraday's constant, pH$_i$ and pH$_o$ the intra- and extracellular pH, Gly-Sar$_i$ and Gly-Sar$_o$, the intra-and extracelluar Gly-Sar concentrations, and z the valency.

Oocytes were initially kept in pH 7.4 medium (96 mM NaCl, 1 mM KCl, 1.8 mM CaCl$_2$, 1.0 mM MgCl$_2$ and 5

Figure 12:
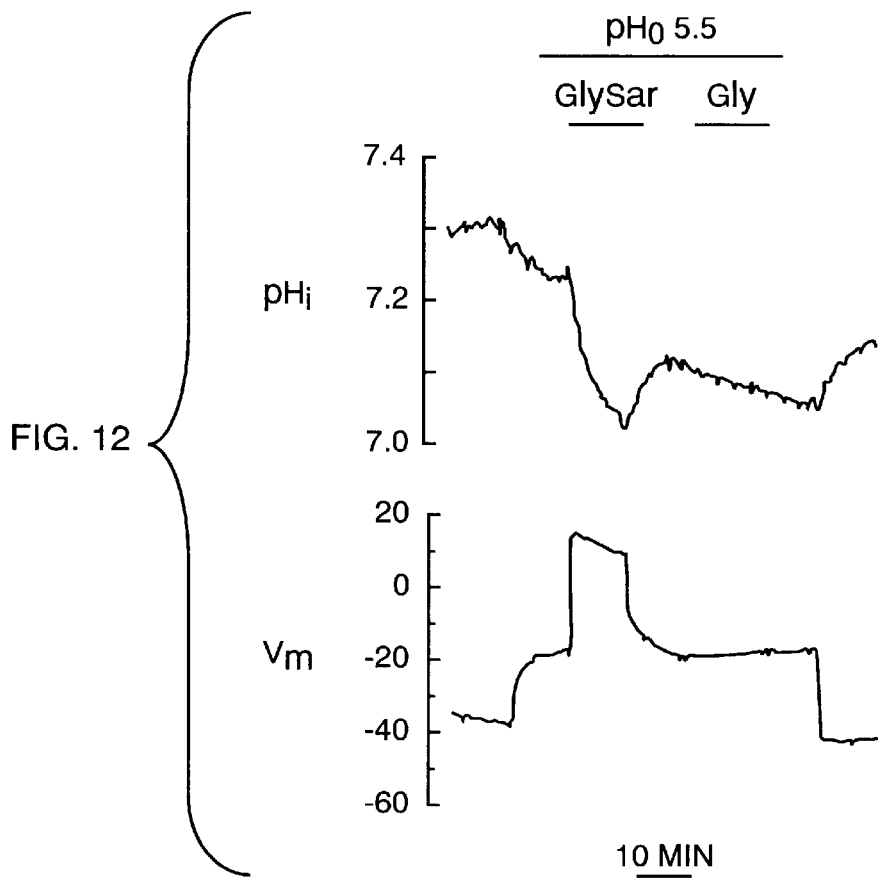
FIG. 12 depicts internal hydrogen concentration and membrane potential of *Xenopus laevis* upon the application of glycyl-sarcosine dipeptide and upon the application of glycine with the exterior pH of such oocytes maintained at 5.5.

HEPES). The switch to a pH 5.5 solution caused a reversible decrease in $pH_i$ that was rapid at first, but slow near the end of the experiment. Application of Gly-Sar (10 mM) in the $pH_o$ 5.5 solution induced a large intracellular acidification and depolarized $V_m$ from −20 mV to +15 mV. In contrast, glycine, which is not an effective substrate for the proton-coupled peptide transporter, evoked no detectable response in both $pH_i$ and $V_m$. In water-injected oocytes, lowering $pH_o$ from 7.4 to 5.5 caused a continuous $pH_i$ decrease which was not dependent on the expression of the proton-coupled peptide transporter. These data is depicted graphically in FIG. 12.

Figure 13:
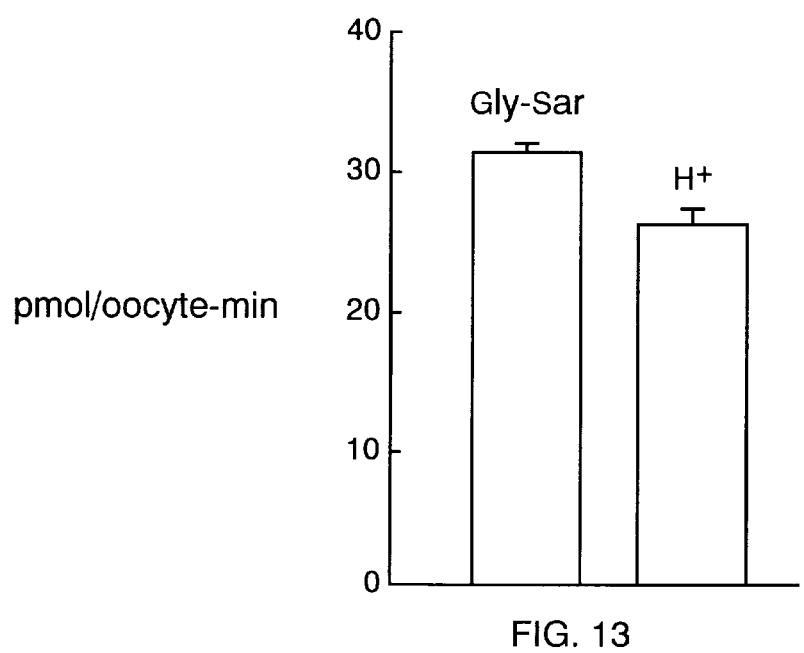
FIG. 13 depicts graphically the initial upgrade of glycyl-sarcosine with the net charge flux.

FIG. 13 depicts in bar graph form the initial uptake of 1 mM glycyl-sarcosine by such oocytes with the net charge flux determined by using glycyl-sarcosine induced inward current as an indicator of hydrogen ion flux. The hydrogen ion to glycyl-sarcosine flux ratio was 1:1.17, indicating that one proton or hydrogen ion is co-transported with each peptide.

Figure 14:
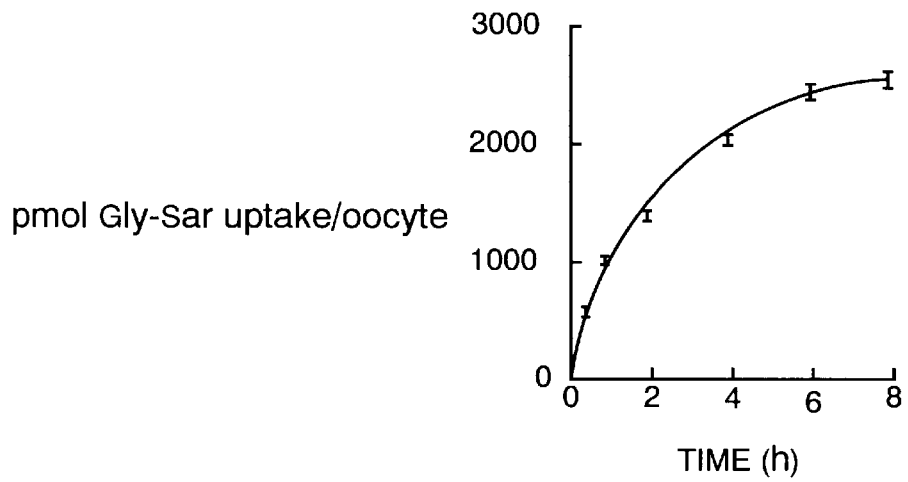
FIG. 14 graphically depicts the time-course of glycyl-sarcosine uptake and reveals that a thermodynamic equilibrium is reached after approximately eight hours.

This 1:1 coupling ratio is consistent with analysis of the coupling ratio based on thermodynamic considerations. Cumulative uptake of $C^{14}$-glycyl-sarcosine was measured as depicted in FIG. 14. These results indicate that after eight hours a thermodynamic equilibrium was reached.

Data represent the average of the uptakes from 20–24 oocytes after subtraction of the uptakes of water-injected oocytes. After a ten hour incubation in 1 mM non-radiolabeled 1 mM glycyl-sarcosine, the $^{14}$C-glycyl-sarcosine influx was 1754±403 (n=7) pmol/oocyte. These data suggest that the transporter was still functional and that equilibrium had been reached. Thin-layer chromatograph of solubilized oocytes incubated in 1 mM $^{14}$C-Gly-Sar (pH 5.5) for seven hours showed that no more than one third of the intracellular $^{14}$C-label represented hydrolyzed glycyl-sarcosine.

EXAMPLE 8

This example describes proton coupled transport of peptides by the proton-coupled peptide transporter independent of membrane potential at pH 5.5. The steady-state current-voltage (I-V) relationship was determined in standard uptake solution at pH 5.5 and at 7.5 under a two-electrode voltage-clamp condition. The membrane potential was held at −50 mV and stepped symmetrically to various test potentials between −150 mV and +50 mV for 100 ms. Glycyl-sarcosine-dependent steady-state currents were obtained as the difference in current measured in the presence and absence of 10 mM glycyl-sarcosine.

Figure 15A:
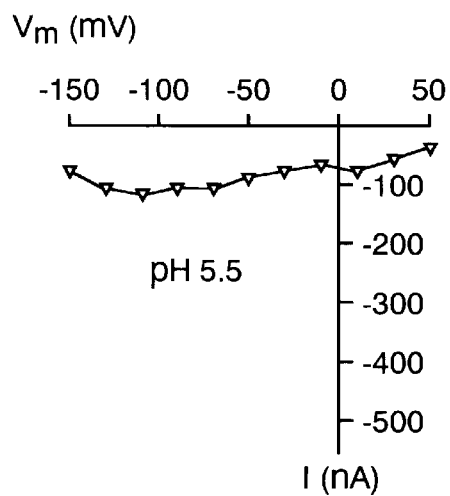
FIGS. 15A and 15B depict steady state current voltage relationships of glycyl-sarcosine coupled hydrogen ion inward current in *Xenopus laevis* oocytes transformed with cRNA coding a proton-coupled peptide transporter at pH 5.5 and 7.4.
Figure 15B:
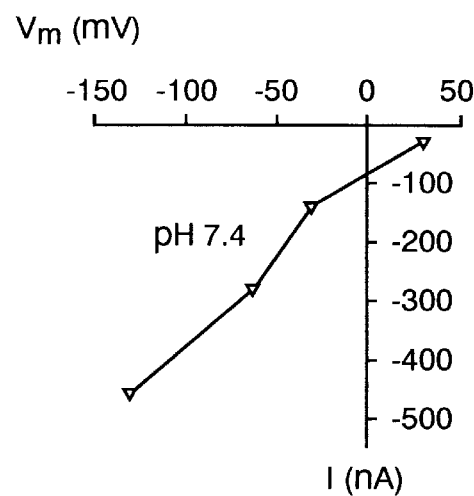

The results which are representative of three experiments, are illustrated in FIG. 15a and b. These results suggest that the proton-coupled peptide transporter is dependent on membrane potential at pH 7.5 but independent of membrane potential at pH 5.5.

The present invention presents novel non-naturally occurring compositions of matter corresponding to a proton-coupled peptide transporter and methods of making and using the same. The compositions and methods have utility in the design of biologically active compositions. The invention has utility to effect transfer of peptides and compounds structurally similar to peptides across cellular membranes, including drugs and other compounds linked to such peptides and structurally similar compounds. Drug linked to a peptide through an N-terminal alpha-amino group is transported across cellular membranes by the proton-coupled peptide transporter and hydrolyzed in cells by the enzyme, prolidase. Hydrolysis releases the active drug from the peptide. In the gut, drug linked to peptide through an N-terminal alpha-amino group is transported at the brush border membrane by epithelial cells having a proton-coupled peptide transporter. In these epithelial cells, the drug linked to a peptide is released by hydrolysis where it diffuses into the blood through the basolateral membrane.

Thus, while preferred embodiments of the present invention have been described, the present invention is capable of variation and modification and, therefore, the invention should not be limited to the precise details set forth, but should include such changes and alterations that fall within the purview of the following claims.

---

I claim:

1. An isolated nucleic acid encoding a proton-coupled peptide transporter, wherein said nucleic acid comprises the sequence SEQ ID NO:1.

2. An isolated proton-coupled peptide transporter comprising a protein having the amino-acid sequence SEQ. I.D. No: 2.

3. A method of transporting a peptide or peptide substitute across a cellular membrane of a cell, the method comprising the steps of:

a. transforming the cell with the nucleic acid of claim 1, the nucleic acid encoding a proton-coupled peptide transporter capable of transporting peptides and peptide substitutes across the cellular membrane, where the transformation of the cell results in functional expression of the transporter; and b. contacting the cell, under conditions favoring transport, to a peptide or peptide substitute capable of being transported by the transporter, thereby resulting in trans-membrane transport of the peptide or peptide substitute as confirmed by comparison with a similarly exposed untransformed cell wherein, said untransformed cell does not comprise a proton-coupled peptide transporter.

4. A method of transporting a peptide or peptide substitute across a membrane preparation, the method comprising the steps of:
   a. transforming a cell with the nucleic acid of claim 1, the nucleic acid encoding a proton-coupled peptide transporter capable of transporting peptides and peptide substitutes across the cellular membrane, where the transformation of the cell results in functional expression of the transporter;
   b. making a membrane from said cell; and
   c. contacting the membrane preparation, under conditions favoring transport, to a peptide or peptide substitute capable of being transported by the transporter, thereby resulting in transmembrane transport of the peptide or peptide substitute as confirmed by comparison with a similarly exposed membrane preparation made from an untransformed cell wherein, said untransformed cell does not comprise a proton-coupled peptide transporter.

* * * * *